United States Patent
Ohiomoba

(10) Patent No.: US 12,205,724 B2
(45) Date of Patent: Jan. 21, 2025

(54) SYSTEMS AND METHODS FOR MACHINE LEARNING-BASED STATE PREDICTION AND VISUALIZATION

(71) Applicant: MARVIN BEHAVIORAL HEALTH INC., Marina del Rey, CA (US)

(72) Inventor: Patrick Ohiomoba, Boston, MA (US)

(73) Assignee: MARVIN BEHAVIORAL HEALTH INC., Marina del Rey, CA (US)

( * ) Notice: Subject to any disclaimer, the term of this patent is extended or adjusted under 35 U.S.C. 154(b) by 0 days.

(21) Appl. No.: 18/168,026

(22) Filed: Feb. 13, 2023

(65) Prior Publication Data

US 2023/0260654 A1 Aug. 17, 2023

Related U.S. Application Data

(63) Continuation of application No. 17/661,530, filed on Apr. 29, 2022, now Pat. No. 11,605,464.
(Continued)

(51) Int. Cl.
*G16H 50/20* (2018.01)
*A61B 5/16* (2006.01)
(Continued)

(52) U.S. Cl.
CPC ............ *G16H 50/20* (2018.01); *A61B 5/165* (2013.01); *G06F 3/04842* (2013.01);
(Continued)

(58) Field of Classification Search
CPC ........ G06F 3/04842; A61B 5/16; G06N 20/00
See application file for complete search history.

(56) References Cited

U.S. PATENT DOCUMENTS 8,700,012 B2    4/2014  Ferren et al.
9,424,532 B1    8/2016  Abedini et al.
(Continued)

OTHER PUBLICATIONS

Clifton B. Parker, "Emotional Fit Important Between a Patient's Desired Feelings and Physician, Stanford Research Shows," Stanford News, Apr. 2, 2015.
(Continued)

*Primary Examiner* — Scott S Trotter
(74) *Attorney, Agent, or Firm* — Ahmann Kloke LLP

(57) ABSTRACT

Obtaining first electronic data of a first user. Obtaining second electronic data for each of a plurality of second users, obtaining first electronic data of a first user. Obtaining second electronic data for each of a plurality of second users. Determining first input data for at least one first machine learning model based on the first electronic data of the first user. Predicting, based on the first input data and the at least one first machine learning model, a first mental state of the first user, the first mental state comprising a set of first mood values, a set of first uncertainty values, and a set of first magnitude values, each first mood value of the set of first mood values being associated with a corresponding first uncertainty value of the set of first uncertainty values and a corresponding first magnitude value of the set of first magnitude values, the first magnitude value indicating a first relative strength or weakness of the associated first mood value. Predicting, based on the first mental state of the first user, the second electronic data for each of the plurality of second users, and one or more second machine learning models, one or more therapeutic matches between the first user and one or more second users of the plurality of second users. Facilitating presentation, via a graphical user interface (GUI), of the one or more therapeutic matches. Receiving, in response to the first user interacting with the GUI, a user selection of a particular second user of the one or more
(Continued)

second users of the plurality of second users. Automatically connecting, in response to receiving the user selection of the particular second user of the one or more second users of the plurality of second users, the first user with each of the one or more second users of the plurality of second users.

20 Claims, 18 Drawing Sheets

Related U.S. Application Data

(60) Provisional application No. 63/267,385, filed on Jan. 31, 2022, provisional application No. 63/182,712, filed on Apr. 30, 2021.

(51) Int. Cl.
  *G06F 3/04842* (2022.01)
  *G06N 20/00* (2019.01)
  *G16H 50/30* (2018.01)
  *G16H 20/70* (2018.01)

(52) U.S. Cl.
  CPC ............. *G06N 20/00* (2019.01); *G16H 50/30* (2018.01); *G16H 20/70* (2018.01)

(56) References Cited

U.S. PATENT DOCUMENTS

| | | |
|---|---|---|
| 9,679,060 B2 | 6/2017 | Hebenthal et al. |
| 10,061,977 B1 | 8/2018 | Chang |
| 10,628,528 B2 | 4/2020 | He et al. |
| 10,643,213 B1 | 5/2020 | Bermudez et al. |
| 2009/0292713 A1 | 11/2009 | Jung et al. |
| 2010/0280579 A1 | 11/2010 | Denison et al. |
| 2010/0305963 A1 | 12/2010 | Firminger et al. |
| 2017/0262606 A1 | 9/2017 | Abdullah et al. |
| 2020/0245949 A1 | 8/2020 | Dagum |
| 2021/0104312 A1 | 4/2021 | Moskowitz |
| 2021/0350917 A1 | 11/2021 | Curtis |
| 2021/0406912 A1 | 12/2021 | Beilis et al. |

OTHER PUBLICATIONS

Dianxi Shi, Xi Chen, Jing Wei, Ruosong Yang, "User Emotion Recognition Based on Multi-class Sensors of Smartphone," IEEE International Conference on Smart City/SocialCom/SustainCom (SmartCity), IEEE Computer Society, pp. 478-485, Dec. 2015.

SYSTEMS AND METHODS FOR MACHINE LEARNING-BASED STATE PREDICTION AND VISUALIZATION

CROSS-REFERENCE TO RELATED APPLICATIONS

The present application is a continuation of U.S. Non-Provisional application Ser. No. 17/661,530 filed on Apr. 29, 2022, entitled "SYSTEMS AND METHODS FOR MACHINE LEARNING-BASED STATE PREDICTION AND VISUALIZATION," which claims priority to U.S. Provisional Patent Application Ser. No. 63/182,712 filed Apr. 30, 2021, entitled "SYSTEMS AND METHODS FOR MACHINE LEARNING-BASED STATE PREDICTION AND VISUALIZATION," and U.S. Provisional Patent Application Ser. No. 63/267,385, filed on Jan. 31, 2022, entitled "SYSTEMS AND METHODS FOR MACHINE LEARNING-BASED PREDICTIVE MATCHING," both of which are hereby incorporated by reference herein.

TECHNICAL FIELD

This disclosure pertains to machine learning. More specifically, this disclosure pertains to machine learning-based predictive matching.

BACKGROUND

Under conventional approaches, computing systems perform user matching using fillable forms. For example, users may complete one or more computer forms (e.g., an online form) and the computing system can compare forms to determine whether any user matches one or more other users. However, such computational matching can be inaccurate and computationally inefficient.

SUMMARY

Various embodiments of the present disclosure include systems, methods, and non-transitory computer readable media configured to obtain first electronic data of a first user. Obtaining second electronic data for each of a plurality of second users. obtaining first electronic data of a first user. Obtaining second electronic data for each of a plurality of second users. Determining first input data for at least one first machine learning model based on the first electronic data of the first user. Predicting, based on the first input data and the at least one first machine learning model, a first mental state of the first user, the first mental state comprising a set of first mood values, a set of first uncertainty values, and a set of first magnitude values, each first mood value of the set of first mood values being associated with a corresponding first uncertainty value of the set of first uncertainty values and a corresponding first magnitude value of the set of first magnitude values, the first magnitude value indicating a first relative strength or weakness of the associated first mood value. Predicting, based on the first mental state of the first user, the second electronic data for each of the plurality of second users, and one or more second machine learning models, one or more therapeutic matches between the first user and one or more second users of the plurality of second users. Facilitating presentation, via a graphical user interface (GUI), of the one or more therapeutic matches. Receiving, in response to the first user interacting with the GUI, a user selection of a particular second user of the one or more second users of the plurality of second users. Automatically connecting, in response to receiving the user selection of the particular second user of the one or more second users of the plurality of second users, the first user with each of the one or more second users of the plurality of second users.

In some embodiments, the systems, methods, and non-transitory computer readable media are further configured to perform determining second input data for at least one first machine learning model based on the second electronic data for each of a plurality of second users; predicting, based on the second input data and the at least one first machine learning model, a respective second mental state of each of the second users of the plurality of second users, each of the respective second mental states comprising a set of second mood values, a set of second uncertainty values, and a set of second magnitude values, each second mood value of the set of second mood values being associated with a corresponding second uncertainty value of the set of second uncertainty values and a corresponding second magnitude value of the set of second magnitude values, the second magnitude value indicating a second relative strength or weakness of the associated second mood value; determining one or more inventories of preferences of the first user, wherein the inventories of preferences include one or more goals of the first user; determining one or more respective goals for each second user of the plurality of second users; obtaining labeled session data associated with a plurality of successful therapeutic matches; generating the one or more second machine learning models based on the first mental state of the first user, the respective second mental state of each of the plurality of second users, the inventory of preferences of the first user, the one or more respective goals for each second user of the plurality of second users, and the labeled session data.

In some embodiments, the first electronic data includes text messages sent by the first user, email messages sent by the first user, voice data of the first user, image data of the first user, and one or more physical orientations of a device of the first user.

In some embodiments, the second electronic data includes text messages sent by the second user, email messages sent by the second user, voice data of the second user, image data of the second user, and one or more physical orientations of a device of the second user.

In some embodiments, the predicting, based on the first mental state of the first user, the second electronic data for each of the plurality of second users, and one or more second machine learning models, one or more therapeutic matches between the first user and one or more second users of the plurality of second users comprises: predicting, based on the first mental state of the first user, a respective second mental state of each of the plurality of second users, the inventory of user preferences of the first user, the one or more goals of the second user, the labeled session data associated with a plurality of successful therapeutic matches, and one or more second machine learning models, one or more therapeutic matches between the first user and one or more second users of the plurality of second users.

In some embodiments, the systems, methods, and non-transitory computer readable media are further configured to perform mapping the set of first mood values, the set of first uncertainty values, and the set of first magnitude values to a first coordinate system, the first coordinate system comprising a plurality of different first mood regions, wherein each of the set of first mood values is mapped to the first coordinate system as a corresponding first user point in the first coordinate system, and wherein each of the corresponding first uncertainty values is mapped as a corresponding first radius originating at the corresponding first point in the first coordinate system; identifying at least a first mood region of the plurality of different first mood regions that includes at least one corresponding user mapped therein; identifying at least a second mood region of the plurality of different first mood regions that does not include any corresponding user points mapped therein, and includes at least a portion of a first radius of the corresponding radii mapped in the coordinate system; and wherein the first mental state of the first user is predicted based on the identified at least a first mood region of the plurality of different first moods regions, the identified at least a second mood region of the plurality of different first mood regions, and the first magnitude values associated with the at least one corresponding user point mapped in the at least a first mood region of the plurality of different first moods regions and the first radius of the corresponding radii mapped in the first coordinate system.

In some embodiments, the systems, methods, and non-transitory computer readable media are further configured to perform mapping the set of second mood values, the set of second uncertainty values, and the set of second magnitude values to a second coordinate system, the second coordinate system comprising a plurality of different second mood regions, wherein each of the set of second mood values is mapped to the second coordinate system as a corresponding second user point in the second coordinate system, and wherein each of the corresponding second uncertainty values is mapped as a corresponding second radius originating at the corresponding second point in the second coordinate system; identifying at least a first mood region of the plurality of different second mood regions that includes at least one corresponding user mapped therein; identifying at least a second mood region of the plurality of different second mood regions that does not include any corresponding user points mapped therein, and includes at least a portion of a second radius of the corresponding radii mapped in the second coordinate system; and wherein the second mental state of the second user is predicted based on the identified at least a first mood region of the plurality of different second moods regions, the identified at least a second mood region of the plurality of different second mood regions, and the second magnitude values associated with the at least one corresponding user point mapped in the at least a first mood region of the plurality of different second moods regions and the second radius of the corresponding radii mapped in the second coordinate system.

In some embodiments, the first coordinate system comprises a two-dimensional coordinate system.

In some embodiments, the second electronic data includes text messages sent by the second user, email messages sent by the second user, voice data of the second user, image data of the second user, and one or more physical orientations of a device of the second user.

In some embodiments, the first coordinate system comprises a three-dimensional coordinate system.

In some embodiments, each first mood value of the set of first mood values is associated with a corresponding point in time.

These and other features of the systems, methods, and non-transitory computer readable media disclosed herein, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for purposes of illustration and description only and are not intended as a definition of the limits of the invention.

DETAILED DESCRIPTION

Figure 1:
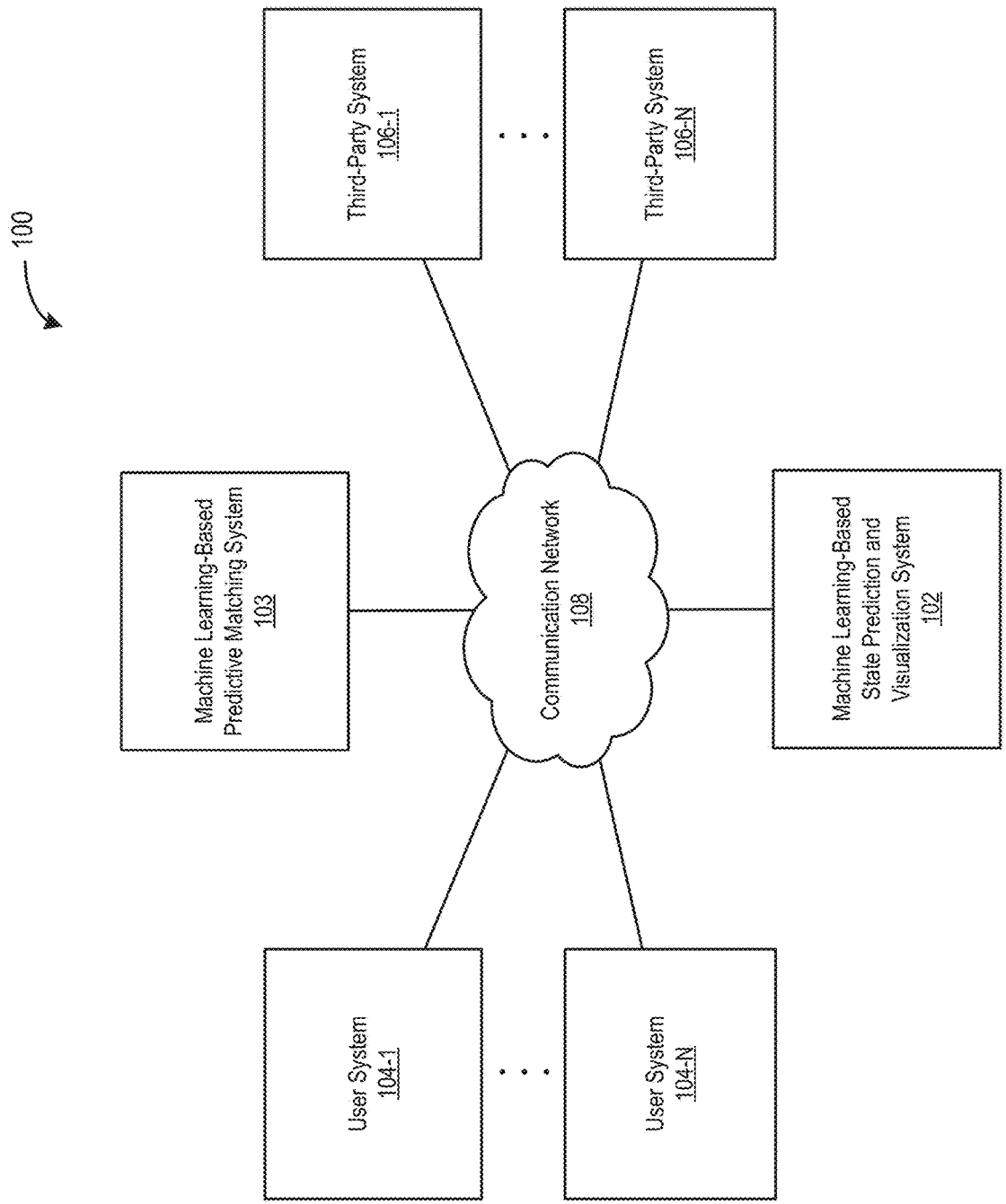
FIG. 1 depicts a diagram of an example system using machine learning to predict mental state and to predict user matches (e.g., therapeutic matches) based on the predicted mental state according to some embodiments.

A claimed solution rooted in computer technology overcomes problems specifically arising in the realm of computer technology. In various embodiments, a computing system is configured to predict a mental state of a first user (e.g., a patient user) based on machine learning, and predict a match (e.g., therapeutic match) and/or alliance (e.g., therapeutic alliance) between the first user and a second user (e.g., a provider user) from a plurality of different second users (e.g., a plurality of provider users). More specifically, the computing system may obtain first electronic data of a first user. For example, the computing system may scan a first user's device (e.g., smartphone) and/or associated first user accounts (e.g., social media accounts) to obtain data from text messages, email messages, social media services (e.g., Facebook), voice data, image data, and/or the like. The computing system may similarly obtain second electronic data of the plurality of second users. For example, the computing system may scan devices (e.g., smartphones) and/or associated user accounts (e.g., social media accounts) of the second users to obtain data from text messages, email messages, social media services (e.g., Facebook), voice data, image data, and/or the like. The computing system may use a first machine learning model to predict a first mental state of the first user based on the obtained first electronic data and predict respective second mental states of the second users based on the obtained second electronic data. In some embodiments, a mental state may be generally defined as a distribution of mood values (or, simply, moods) over time. For example, mood values may include "angry," "sad," "happy," and/or other predefined or otherwise generally understood moods. Accordingly, it will be appreciated that, in some embodiments, a mood value is discrete, while a mental state is contiguous. The computing system, based on the predicted mental state(s) of the first user and/or the second users, can intelligently predict a match between the first user and one or more of the second users using another machine learning model. For example, the computing system can provide the predicted mental state(s) of the first user and/or the second users to the machine learning model, and the machine learning model can output a value indicative of a successful or unsuccessful match.

Accordingly, the computing system may provide a technological benefit over traditional systems which are typically limited to comparing and/or filtering computerized forms. More specifically, the computing system can be more computationally efficient (e.g., in terms of processing, memory, graphical display, and/or rendering) relative to traditional systems because it utilizes particular machine learning models and/or machine learning model input data. Furthermore, the computing system provides more accurate matching through a particular structure of machine learning models and machine learning approaches.

FIG. 1 depicts a diagram of an example system 100 using machine learning to predict mental state and to predict user matches (e.g., therapeutic matches) based on the predicted mental state according to some embodiments.

In the example of FIG. 1, the system 100 includes a machine learning-based state prediction and visualization system 102, a machine learning-based predictive matching system 103, user systems 104-1 to 104-N (individually, the user system 104, collectively, the user systems 104), third-party systems 106-1 to 106-N (individually, the third-party system 106, collectively, the third-party systems 106), and a communication network 108.

The machine learning-based state prediction and visualization system 102 may function to predict one or more mental states of one or more uses (or set of users) based on machine learning. For example, users can include patient users (e.g., a medical patient, potential medical patient, mental health patient, potential mental health patient), provider users (e.g., medical provider, potential medical provider, mental health provider, potential mental health provider), and/or other service recipient users and service provider users. Although patient users and provider users are primarily discussed herein, it will be appreciated that the systems and methods described herein can also be applied to other types of users.

In some embodiments, the machine learning-based state prediction and visualization system 102 may function to select, arrange, manage, visualize, and/or otherwise manipulate and/or facilitate presentation of graphical elements (e.g., emojis), and/or other types of emotional indicators, based on the machine learning-predicted mental state of the user. In various embodiments, functionality of the machine learning-based state prediction and visualization system 102 may be performed by one or more servers (e.g., a cloud-based server) and/or other computing devices. The machine learning-based state prediction and visualization system 102 may be implemented by a cloud-computing platform.

In some embodiments, graphical elements can be a type of emotional indicator, and the systems and methods described herein can operate on (e.g., select, arrange, manipulate, and/or the like), and otherwise utilize, emotional indicators in the same manner as graphical elements. Thus, for example, the system 100 may use machine learning to predict mental state and to select, arrange and/or otherwise manipulate emotional indicators based on the predicted mental state. Emotional indicators can include graphical elements (e.g., emojis), audio elements (e.g., voices), haptic elements, video elements, animation elements, and/or the like. Thus, in some embodiments, the systems and methods described herein can predict mental state as described in this paper in order to select, arrange, manage, manipulate, visualize, facilitate presentation, and/or perform any of the other functions described herein, for any type of emotional indicator in the same or similar manner as graphical elements.

In some embodiments, the machine learning-based state prediction and visualization system 102 may function to scan and/or other obtain electronic data from user systems (e.g., user systems 104, discussed below) and/or third-party systems (e.g., third-party systems 106, discussed below). For example, the machine learning-based state prediction and visualization system may scan text messages, email messages, voice data, image data, and/or the like. The machine learning-based state prediction and visualization system 102 may use some or all of this electronic data to provide input to a machine learning model that predicts a mental state of the user based on the input.

In some embodiments, the machine learning-based state prediction and visualization system may function to select, arrange, manage, visualize, and/or otherwise facilitate presentation of one or more graphical elements (e.g., emojis), and/or other types of emotional indicators, through a graphical user interface based on one or more predicted mental states. For example, the machine learning-based state prediction and visualization system may facilitate a mobile application executing on a user system to present a set of emojis associated with the predicted mental state, rather than merely presenting a general list of emojis or the most commonly used or most recently used emojis.

The machine learning-based predictive matching system 103 may function to predict matches and/or alliances between users (e.g., patient users and provider users) based on one or more predicted mental states of one or more users (e.g., a patient user, provider users) using machine learning.

In some embodiments, the machine learning-based predictive matching system 103 predicts a therapeutic match or a therapeutic alliance between one or more users (e.g., a patient user) and one or more provider users from a set of different provider users. As used herein, an alliance can be a cooperative working relationship between users (e.g., between a patient user and a provider user). It will be appreciated that reference to a "match" herein can include and/or consist of an alliance.

The user systems 104 may function to receive, transmit, and/or present (e.g., display) information. For the example, the user systems 104 may generate and/or present graphical user interfaces that a user may interact with. In various embodiments, functionality of the user systems 104 may be performed by one or more devices (e.g., smartphones, laptop computers, desktop computers, tablets, servers) and/or other computing devices. In some embodiments, the user systems 104 may be user systems of patient users (e.g., mental health patient and/or other medical patient) and/or provider users (e.g., therapists and/or other medical provider).

In some embodiments, the user systems 104 may function to receive, transmit, obtain, and/or present electronic data of a user and/or associated with a user. For example, electronic data may include texts messages (e.g., SMS messages, iMessages, and/or the like), email messages, social media data (e.g., data from a user's social media account), voice data (e.g., audio recording a user speaking, a voicemail messages, a phone or video call, and/or the like), image data (e.g., a picture of user, a video of a user), haptic data (e.g., pressure from user's hand holding a device), physical location data (e.g., GPS data), physical orientation data (e.g., a physical orientation of device of user at the time other electronic data is captured or other time), and/or the like. In some embodiments, electronic data may include encrypted data (e.g., data from an encrypted text message communication) and/or decrypted data.

The third-party systems 106 may function to receive, transmit, and/or present information. For example, the third-party systems 106 may comprise social media systems (e.g., Facebook, Instagram, TikTok, LinkedIn, email systems, text messages systems, and/or the like). In some embodiments, functionality of the third-party systems 106 may be performed by one or more servers (e.g., cloud-based servers) and/or other computing devices.

The communications network 108 may represent one or more computer networks (e.g., LAN, WAN, or the like) or other transmission mediums. The communication network 108 may provide communication between systems 102-106 and/or other systems and/or components thereof (e.g., engines and/or datastores of the systems 102-106) described herein. In some embodiments, the communication network 108 includes one or more computing devices, routers, cables, buses, and/or other network topologies (e.g., mesh, and the like). In some embodiments, the communication network 108 may be wired and/or wireless. In various embodiments, the communication network 108 may include the Internet, one or more wide area networks (WANs) or local area networks (LANs), one or more networks that may be public, private, IP-based, non-IP based, and so forth.

Figure 2:
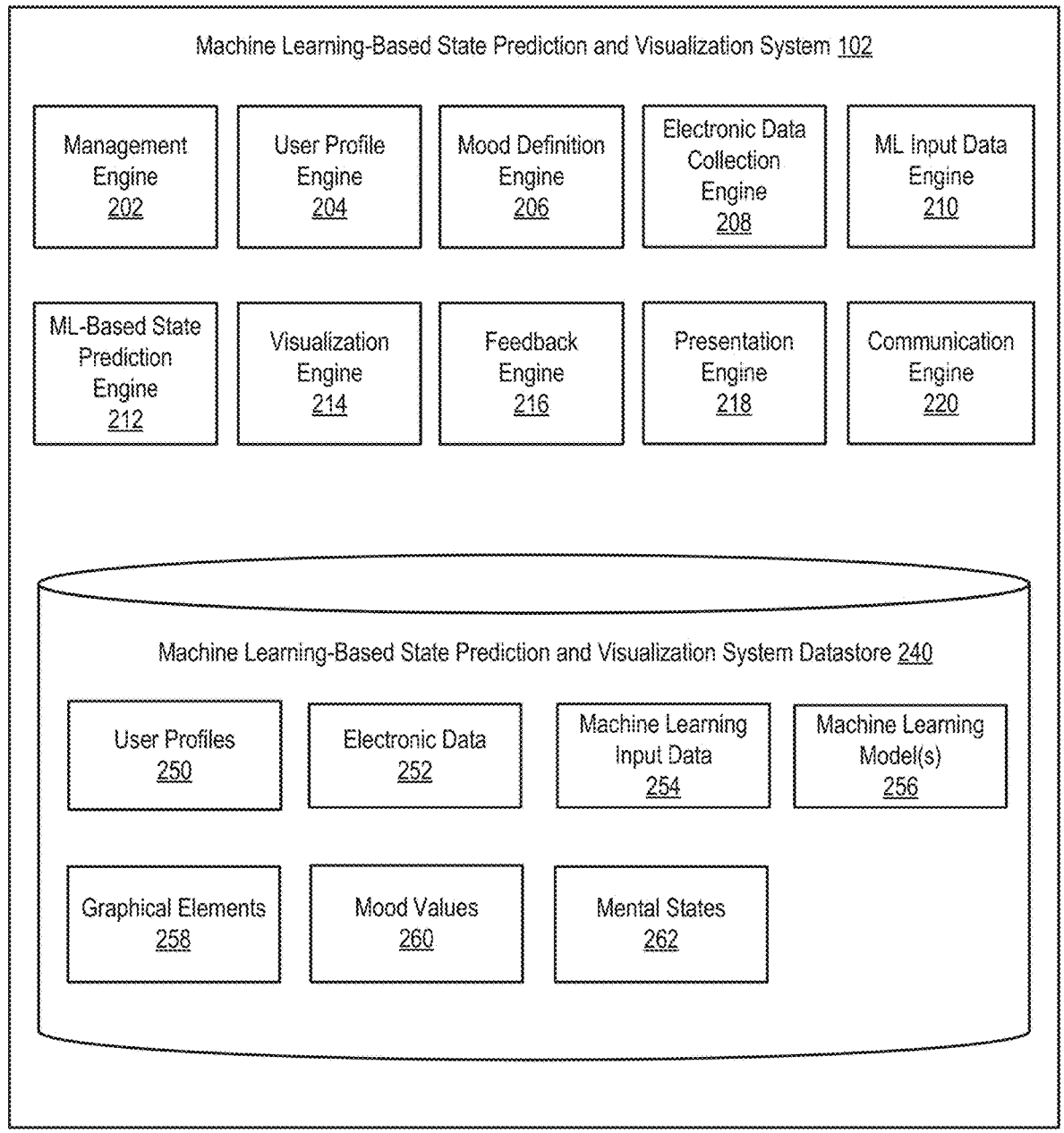
FIG. 2 depicts a diagram of an example machine learning-based state prediction and visualization system according to some embodiments.

FIG. 2 depicts a diagram of an example machine learning-based state prediction and visualization system 102 according to some embodiments. In the example of FIG. 2, the machine learning-based state prediction and visualization system 102 includes a management engine 202, a mood definition engine 206, an electronic data collection engine 208, a machine learning input data 210, a machine learning-based state prediction engine 212, a visualization engine 214, a feedback engine 216, a presentation engine 218, a communication engine 220, and a machine learning-based state prediction and visualization system datastore 240.

The management engine 202 may function to manage (e.g., create, read, update, delete, or otherwise access) user profiles 250, electronic data 252, machine learning input data 254, machine learning model(s) 256, graphical elements 258, and/or mood values 260 (or, simply, "moods"). The management engine 202 can perform any of these operations manually (e.g., by a user interacting with a GUI) and/or automatically (e.g., triggered by one or more of the engines 204-220). Like the other engines described herein, some or all the functionality of the management engine 202 can be included in and/or cooperate with one or more other engines (e.g., engines 204-220) and datastores (e.g., machine learning-based state prediction and visualization system datastore 240).

The user profile engine 204 may function to register users (e.g., user "John Smith"), register associated user systems 104 (e.g., a mobile device of user John Smith), register user accounts (e.g., John Smith's accounts of third-party systems 106), and/or generate user profiles 250. In one example, users can include patient users, provider users (e.g., medical provider or other service provider). User profiles 250 may include some or all of the following information:

User Profile Identifier: identifies the user profile.
User Identifier: identifies the user.
User Credentials: username, password, two-factor authentication, and/or other credentials.
User Personal Information: identifies the user's name, contact information (e.g., email address, phone number, mailing address).
Registered (or, associated) User Systems: Identifies user systems 104 associated with the user.
Registered (or, associated) Accounts and/or Third-Party Systems: identifies user accounts (e.g., social media accounts), and associated access information (e.g., APIs, user account names and credentials, and/or the like).
Mood History: History of identified moods for the user and associated time stamps.
Mental State History: history of mental states predicted by the machine learning-based state prediction and visualization system for the user, and associated timestamps.
Current Mental State: a current mental state of the user predicted by the machine learning-based state prediction and visualization system.
Historical User Selections: Historical selections of graphical elements selected by the user.
Inventories of Preferences: inventories of preferences (e.g., C-CNIP, URICA) of the user. This can include the questions and/or answers of the inventories of preferences, and/or inventory scores (e.g., default inventory score and/or tunes inventory score).
Goals (or, Criteria): Goals and/or criteria of the user. This may be included in the inventories of preferences, and/or based on the inventories of preferences. This may also be supplemental of the inventories of preferences.
User Privacy Settings: identifies which electronic data 250, or types of electronic data (e.g., text messages), may be used for predicting mental state.
Electronic data: electronic data 252 obtained by the machine learning-based state prediction and visualization system 102, and/or references (e.g., pointers, links)

to electronic data 252 obtained by the machine learning-based state prediction and visualization system.

In various embodiments, the user profiles 250 may be used by some or all of the engines described herein to perform their functionality described herein.

The mood definition engine 206 may function to define and/or generate moods. Moods may be identified by mood values. For example, mood values may be alphanumeric text describing a mood (e.g., "angry"), a numeric value, and/or hash values (e.g., for faster indexing, access, and/or the like). As used in this paper, moods are distinct from mental states. For example, moods may be discrete, while mental states may be contiguous, as discussed elsewhere in this paper. In some embodiments, the mood definition engine 206 defines moods as predetermined definitions that are generally accepted and understood. For example, the mood definition engine 206 may define an angry mood, a sad mood, a happy mood, and/or the like. These moods are discrete and have a generally understood definition.

Figure 5A:
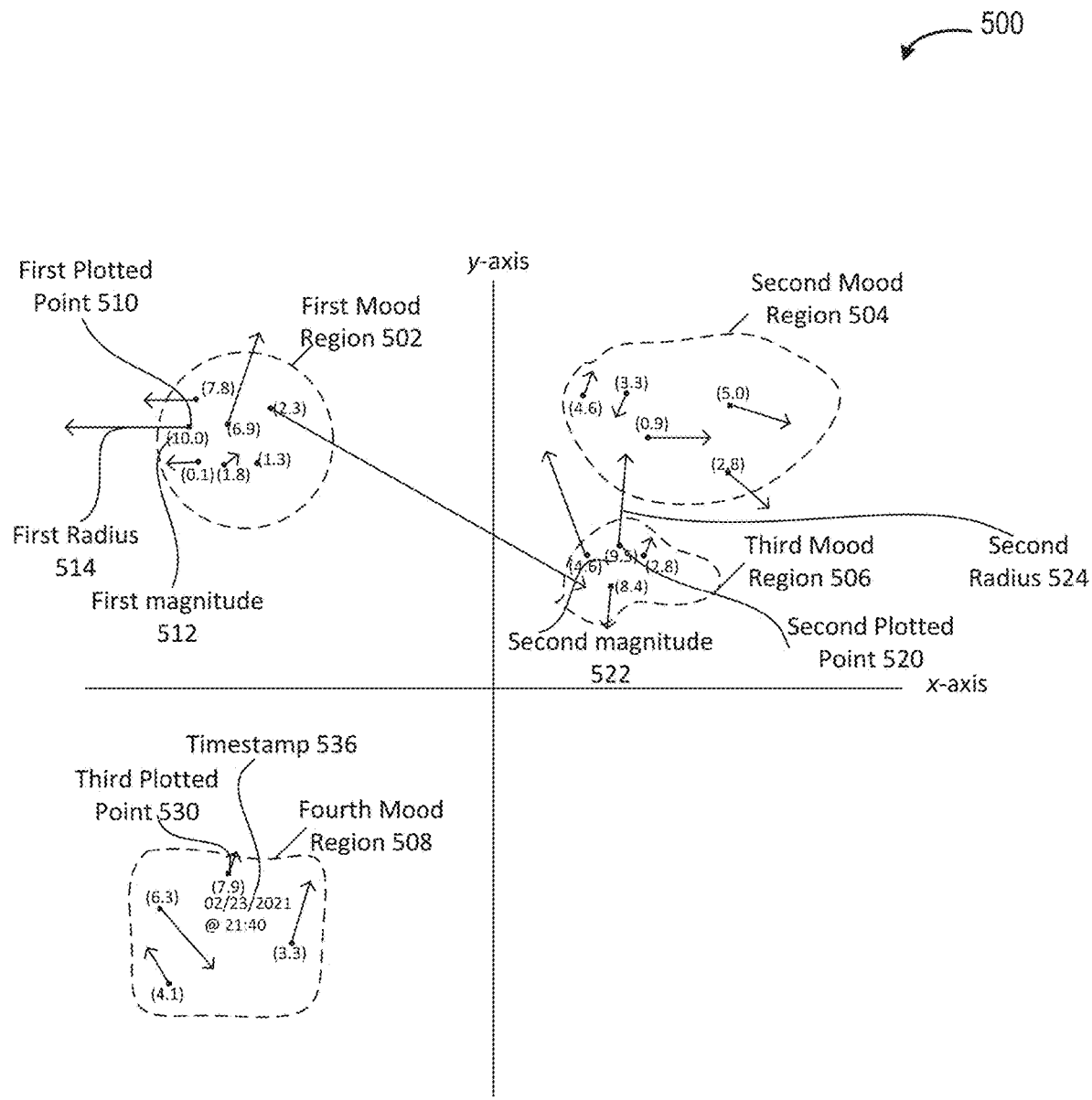
FIG. 5A depicts an example two-dimensional coordinate system representing an example mental state according to some embodiments.
Figure 5B:
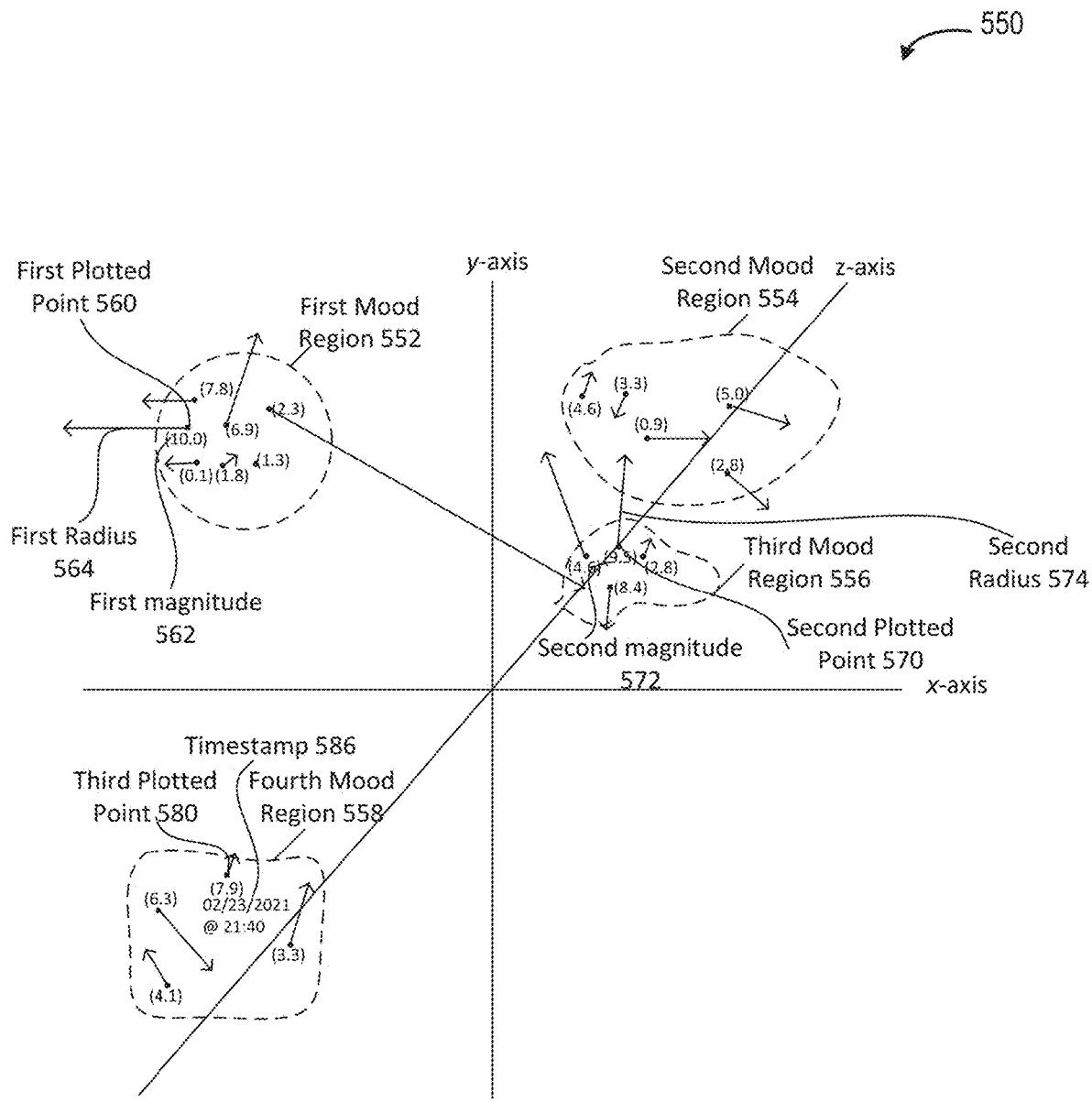
FIG. 5B depicts an example three-dimensional coordinate system representing an example mental state according to some embodiments.

In some embodiments, the mood definition engine 206 defines a mood as one or more regions of a coordinate system and/or space (or, simply, coordinate system). As used in this paper, coordinate systems are multi-dimensional (e.g., two-dimensional, three-dimensional, four-dimensional, and/or the like). In some embodiments, the boundaries of the regions may be manually defined and/or automatically defined by the mood definition engine 206. For example, an administrator may manually define the boundaries of the regions for some or all of the different moods. In another example, the mood definition engine 206 may automatically define mood regions based on known and/or labeled data (e.g., electronic data 252, machine learning input data 254). For example, data may be labeled for individuals with known moods, and those known moods may be plotted in the coordinate system. The plotted points may be used by the mood definition engine 206 to construct the boundaries of the mood regions. FIGS. 5A and 5B show example coordinate systems and example mood regions associated with different moods.

The electronic data collection engine 208 may function to collect, gather, and/or otherwise obtain electronic data 252 (e.g., from user systems 104 and/or third-party systems 106). For example, electronic data 252 may include texts messages (e.g., SMS messages, iMessages, and/or the like), email messages, social media data (e.g., data from a user's social media account), voice data (e.g., audio recording of a user speaking, voicemail messages, a phone or video call, and/or the like), image data (e.g., a picture of user, a video of a user), haptic data (e.g., pressure from user's hand holding a device), physical location data (e.g., GPS data), physical orientation data (e.g., a physical orientation of device of user at the time other electronic data is captured or other time), express statements by a user (e.g., an express indication of mood by a user in a text message or other electronic data 252), and/or the like. The electronic data 252 can be data associated with different types of users (e.g., patient users, provider users) and/or associated devices.

In some embodiments, the electronic data collection engine 208 may scan associated user systems 104 for local electronic data 252 (e.g., text messages that are local to a user system 104, email messages that are local to a user system 104), remote electronic data 252 (e.g., cloud-stored text messages, cloud-stored email messages, social media data) to obtain the electronic data 252. The electronic data collection engine 208 may use information from an associated user profile 252 (e.g., user credentials) and/or APIs to obtain the electronic data 252. For example, the electronic data collection engine 208 may use APIs to obtain electronic data 252 from Facebook, email servers, text message servers, and/or the like, in addition to obtaining data stored locally on user systems 104. In some embodiments, the electronic data 252 obtained by the electronic data collection engine 208 for various users may be limited and/or otherwise controlled by associated user profiles 250. For example, a user may specify in the privacy settings of their user profile 250 that only local data may be used, only data to or from certain recipients may be used, only data from a certain time period may be used, only specifically selected data or types of data (e.g., text messages) may be used, and/or the like.

In some embodiments, the electronic data collection engine 208 may obtain electronic data 252 in real-time and/or periodically. For example, the electronic data collection engine 208 may obtain electronic data 252 as it is entered by a user (e.g., as a user inputs a text message into a user system 104). In another example, the electronic data collection engine 208 may periodically obtain (e.g., once an hour, once a day, and/or the like) electronic data 252. It will be appreciated that obtaining the electronic data 252 may comprise obtaining the actual original electronic data, a copy of the original electronic data, a reference (e.g., pointer, link) to the original electronic data, a reference to a copy of the original electronic data, and/or the like. Accordingly, it will be appreciated that references to electronic data may be operated on by the machine learning-based state prediction and visualization system 102 to achieve the same or similar results as operating on the actual electronic data 252 itself.

In some embodiments, the electronic data collection engine 208 may collect electronic data 252 directly from a user (e.g., an explicit indication of a mood). For example, the electronic data collection engine 208 may prompt the user for their mood in response to a trigger event. For example, trigger events may be based on identified keywords of electronic data 252, time-based triggers, and/or the like. In another example, a user may initiate providing an explicit indication of their mood to the machine learning-based state prediction and visualization system 102.

In some embodiments, a user system (e.g., user system 104) includes some or all of the functionality of the electronic data collection engine 208 and/or functions to cooperate with the electronic data collection engine 208 to perform some or all of the functionality thereof. For example, an application (e.g., mobile application) executing on a user system 104 may itself, and/or in cooperation with the electronic data collection engine 208, obtain electronic data 252. Similarly, in some embodiments, functionality of other engines and/or components of the machine learning-based state prediction and visualization system 102 can be performed by one or more other systems (e.g., user systems 104) and/or in cooperation with those one or more other systems. In some embodiments, the machine learning-based state prediction and visualization system 102 comprises a server system and the user systems 104 comprise client systems of the machine learning-based state prediction and visualization system 104. In some embodiments, some or all of the functionality of the machine learning-based state prediction and visualization system 104 can be implemented as part of a user system (e.g., as a mobile application executing the user system 104).

The machine learning input data engine 210 may function to generate input data 254 for one or machine learning models 256. The machine learning input data engine 210 may generate the machine learning input data 254 based on some or all of the electronic data 252. For example, the machine learning input data engine 210 may generate machine learning input data 254 based on some or all of the electronic data 252 associated with a particular user (e.g., user John Smith). In some embodiments, the machine learning input data engine 210 may normalize the electronic data 252 to a normalized data format, and the normalized data format may comprise the data format of the machine learning input data 254. This may allow, for example, the machine learning-based state prediction and visualization system 102 to obtain data from a variety of different sources regardless of their original format and allow the machine learning-based state prediction and visualization system 102 to operate on the data regardless of the original format.

In some embodiments, the machine learning input data engine 210 selects a subset of electronic data 252 associated with a particular user. For example, the machine learning input data engine 210 may select the subset of electronic data 252 based on privacy setting of an associated user profile 250. In another example, the machine learning input data 210 may select representative electronic data 252 in order to reduce an amount of data provided to the machine learning model 256, and/or prevent or reduce the likelihood of providing stale data to the machine learning model 256. For example, the machine learning input data engine 210 may perform the selection based on user history. Accordingly, the machine learning input data engine 210 may select only electronic data 252 within the past month for one user (e.g., because there is a relatively large amount of data for that user), while the machine learning input data engine 210 may select data within the past year for another user (e.g., because there is a relatively little amount of data for that user).

In some embodiments, the machine learning input data engine 210 may select a subset of electronic data 252 based on one or more rules. For example, rules may define time periods of data to be used (e.g., within the last month), type of data to be used (e.g., only text messages), and/or the like. Different rules may be manually and/or automatically defined for different users. For example, based on the feedback received from particular users (as discussed elsewhere herein), the machine learning input data engine 210 may determine that particular types are electronic data 252 (e.g., email messages) are not effective in predicting mental state for a particular user, while feedback received from other users may indicate that those types of electronic data 252 are effective in predicting mental state for other users. Accordingly, the machine learning input data engine 210 may filter out ineffective types of electronic data 252 for some users, while not filtering those types of electronic data 252 for other users.

In some embodiments, the machine learning input data engine 210 may identify, define, determine, and/or analyze (collectively, analyze) features of electronic data 252 to predict mental state. For example, the machine learning-based state prediction engine 212 may analyze features of voice data of electronic data 252 to predict mental state. Voice data may include recordings of phone or video calls, voicemail messages, ambient voice data (e.g., of the user speaking in the vicinity of a user system 104 that may capture the voice data), and/or the like. The machine learning input data engine 210 may analyze features of the voices in the voice data (e.g., voice of the user and/or others) to identify stress, tension, moods, and/or the like. For example, the machine learning input data engine 210 may include digital signal processing elements in order to facilitate analysis of voice data and/or other electronic data 252. This analysis and/or features may be used by the machine learning model 256 to facilitate prediction of a user's mental state.

In another example, the machine learning input data engine 210 may analyze image data (e.g., pictures or video of a user or other individuals, such as individuals the user is communicating with) to predict mental state. In some embodiments, the machine learning input data engine 210 may use digital signal processing and/or facial recognition to scan images for features indicating stress, tension, moods, and/or the like. This analysis and/or features may be used by the machine learning model 256 to facilitate prediction of a user's mental state.

In another example, the machine learning input data engine 210 may include optical character recognition, regular expressions, and/or natural language processing elements to facilitate mental state prediction. For example, optical character recognition, regular expressions, and/or natural language processing elements may be used to analyze features of a text messages, email messages, social media data, and/or the like, to facilitate prediction of mental state.

The machine learning-based state prediction engine 212 may function to predict mental states of users. In some embodiments, the machine learning-based state prediction engine 212 predicts mental state using one more machine learning models 256 and machine learning input data 254. For example, the machine learning models 256 may include Bayesian models, neural networks models, deep learning models, supervised learning models, unsupervised learning models, random forest models, and/or the like.

In one example, the system can have a distribution of moods with magnitudes and uncertainties at one point in time. In some embodiments, the mental states can be temporal representations of such distributions at several different points in time. Accordingly, such mental states can efficiently capture both the time scope of complex behaviors as well as any relevant uncertainties.

In some embodiments, a mental state may be defined as a set of mood values, a set of uncertainty values, and a set of a magnitude values. Each mood value of the set of mood values may be associated with a corresponding uncertainty value of the set of uncertainty values and a corresponding magnitude value of the set of magnitude values. The magnitude value may indicate a relative strength and/or weakness of the associated mood value. In some embodiments, a predicted mental state of the user (e.g., at a particular point of time and/or a particular period of time) may be stored in a user profile 250 and/or the datastore 240 as mental states 262. The aforementioned definition of a mental state is one example of a mental state, and may be referred to as one example of a triplet. The triplet may be stored in a data object, and/or as table data. In some embodiments, triplets may be stored in a dynamic data object. For example, the dynamic data object may automatically resize depending on the amount of triplet data being stored. This may allow, for example, the machine learning-based state prediction and visualization system to function more efficiently.

In some embodiments, the mental state is defined as a mapping of the triplet to a coordinate system. For example, each mood of the triplet may be plotted in various mood regions of the coordinate system, and the distribution of those plots over time may be the predicted mental state of a user. Each mood may be associated with a particular point in time (e.g., as captured by a timestamp). Accordingly, a mental state may be considered to be contiguous, while a mood may be considered to be discrete. Furthermore, while moods are typically predefined, mental states typically are not predefined. For example, while the machine learning-based state prediction engine 212 may recognize and/or define general categories of mental state (e.g., depressed, bipolar, and/or the like), the predicted mental states themselves may be unique. Accordingly, two different users may have different mental states (e.g., as indicated by their respective mappings) but fall within the same category of mental state (e.g., depressed). This may be significant because the selection and arrangement of graphical elements, as discussed elsewhere herein, may be based on the predicted mental state of the user, and not necessarily upon an associated category of mental state. Accordingly, two users that may be predicted to fall into a depressed category, may nonetheless be presented with a different selection and/or arrangement of graphical elements. In other embodiments, graphical elements may be presented based on a category of mental state instead of, or in addition to, the predicted mental state.

In some embodiments, the uncertainty value represents a predicted accuracy value of the associated mood value. For example, an uncertainty value may be a numerical value (e.g., between 0-10), a percentage value, and/or the like. The uncertainty value may range from no uncertainty (e.g., because the user expressly indicated that they are angry) to highly uncertain (e.g., there was a relatively small amount of electronic data 252 or machine learning input data 254). In some embodiments, the uncertainty value may be referred to as a variance, and it may be represented as a radius (or, radii) originating from the corresponding plotted point associated with the mood. The uncertainty value may be represented as a feature of the mapped radius. For example, a shorter length radius may indicate a lower uncertainty value, and a longer length radius may indicate a higher uncertainty value.

In some embodiments, the machine learning-based state prediction engine 212 may predict uncertainty values based on the machine learning input data 254. If there is a relatively large amount of machine learning input data 254 to be provided to the machine learning model 256 to predict the user's mental state, the uncertainty values may be relatively low. Conversely, if there is a relatively small amount of machine learning input data 254 to be provided to the machine learning model 256 to predict the user's mental state, the uncertainty values may be relatively high. Similarly, if the machine learning model 256 has a relatively large amount of labeled data similar to machine learning input data 254, then uncertainty values may be relatively low, while if the machine learning model 256 has a relatively small amount of labeled data similar to the machine learning input data 254, then the uncertainty values may be relatively high.

In some embodiments, plotted points that indicate a user's mood (e.g., for the purpose of predicting the user's mental state) may be referred to as "user points" of the coordinate system. The coordinate system may also include other plotted points, as well. For example, the coordinate system may include plotted points of moods of other individuals (e.g., based on labeled data). The distance between a user point and another plotted point may be used to predict and/or adjust the uncertainty value. For example, a user point near another plotted point may be assumed to be more accurate, and may result in a lower uncertainty value, while a user point relatively far away from another plotted point may be assumed to be less accurate and may result in a higher uncertainty value.

In some embodiments, the radius representing the uncertainty value may extend from a point in a particular mood region (e.g., an angry region) into one or more other mood regions (e.g., a sad region). In such instances, this may allow the machine learning-based state prediction engine 212 to base the mental state prediction not only on the plotted mood region (e.g., angry mood region), but also on the one or more other mood regions as well (e.g., the sad mood region).

In some embodiments, the magnitude value may be a numerical value (e.g., between 0-10), a percentage value, and/or the like. As indicated elsewhere herein, the magnitude value may indicate a relative strength and/or weakness of an associated mood. For example, a mental state may include an angry mood value with relatively high magnitude (e.g., 8 on a scale of 0-10), and a relatively low uncertainty value (e.g., 2 on a scale of 0-10). Accordingly, anger may be relatively larger impact on the overall predicted mental state relative to other moods of the user that have lower magnitudes and/or higher uncertainty values.

In some embodiments, a mental state may include a second uncertainty value representing a predicted accuracy of an associated magnitude value. This second uncertainty value may be mapped to a coordinate system as a second radius (or radii) originating from the plotted user point.

In some embodiments, the machine learning-based state prediction engine 212 may output one or more vector values (e.g., output from a machine learning model 256) corresponding to a triplet. The machine learning-based state prediction engine 212 may map a triplet to a coordinate system. In some embodiments, the mapping of a triplet to a coordinate system is a mental state. In other embodiments, the triplet itself is a mental state.

In some embodiments, the machine learning-based state prediction engine 212 may predict mental state based on physical orientation of a user system 104. The physical orientation may include angle, tilt, and/or the like, relative to the user and/or another feature (e.g., another person in which a user is communicating, or the ground surface). For example, if the physical orientation indicates that a top portion of a user system 104 is points towards the ground, the machine learning-based state prediction engine 212 may use that as an indicator of one or more particular moods (e.g., a sad mood), while a physical orientation of a top portion of the user system 104 pointing away from the ground may be used as an indicate of one or more other moods (e.g., a happy mood).

The visualization engine 214 may function to select, arrange, and/or otherwise organize (collectively, organize) graphical elements (e.g., emojis) based on predicted mental state. For example, graphical elements may be static, animated, include audio elements, video elements, haptic elements, and/or the like. In some embodiments, the visualization engine 214 may organize a subset of graphical elements from a set of graphical elements based on a mental state of a user in order to present an intelligently and computationally efficient organization of graphical elements through a graphical user interface (e.g., a text message interface of a text messaging application executing on a user system 104). More specifically, the visualization engine 214 may organize graphical elements based on a triplet and/or a mapping of a triplet on a coordinate system.

As discussed elsewhere herein, mental states typically are not predefined. For example, while the machine learning-based state prediction engine 212 may recognize and/or define general categories of mental state (e.g., depressed, bipolar, and/or the like), the predicted mental states themselves may be unique. Accordingly, two different users may have different mental states (e.g., as indicated by their respective mappings) but fall within the same category of mental state (e.g., depressed). The visualization engine 214 may organize the subset of graphical elements based on the predicted mental state of the user, and not necessarily upon associated category of mental state. Thus, two different users that may be predicted to fall into a "depressed" mental category, may nonetheless be presented with a different organization of graphical elements.

In some embodiments, the visualization engine 214 may use an additional layer of machine learning to organize graphical elements. For example, a first layer of machine learning may be used by the machine learning-based state prediction engine 212 to predict mental state, while a second layer of machine (e.g., using different and/or the same machine learning model 256 as the machine learning-based state prediction engine 212) may be used to organize graphical elements based on the predicted mental state. For example, a predicted mental state 260 may be provided as input to a second machine learning model 256, and the output may comprise a vector value that may be used to organize a subset of graphical elements. In some embodiments, the second model may be based on labeled data associating particular graphical elements with particular predicted mental states that have been verified (e.g., manually prior to model deployment and/or by the feedback engine 216, discussed below).

The feedback engine 216 may function to train, refine, and/or otherwise improve the machine learning and/or machine learning models 256 described herein. In some embodiments, the feedback engine 216 receives user selections of graphical elements presented to a user based on the user's predicted mental state. For example, a user selection from a subset of graphical elements presented to the user based on their predicted mental state may indicate that the machine learning model is performing accurately. In another example, a user selection of a graphical element that was not included in the subset of graphical elements presented to the user based on their predicted mental state may indicate that the machine learning model needs improvement and/or correction (e.g., due to concept drift). The feedback engine 216 may utilize the user selections to adjust parameters of the machine learning model 256, and/or otherwise train, retrain, refine, and/or improve the corresponding machine learning and/or machine learning models 256.

The presentation engine 218 may function to present visual, audio, and/or haptic information. In some embodiments, the presentation engine 218 generates graphical user interfaces, and/or components thereof (e.g., server-side graphical user interface components) that can be rendered as complete graphical user interfaces on remote systems (e.g., user systems 104).

The communication engine 220 may function to send requests, transmit and receive communications, and/or otherwise provide communication with one or more of the systems, engines, devices and/or datastores described herein. In a specific implementation, the communication engine 220 may function to encrypt and decrypt communications. The communication engine 220 may function to send requests to and receive data from one or more systems through a network or a portion of a network (e.g., communication network 108). In a specific implementation, the communication engine 220 may send requests and receive data through a connection, all or a portion of which can be a wireless connection. The communication engine 220 may request and receive messages, and/or other communications from associated systems and/or engines. Communications may be stored in the machine learning-based state prediction and visualization system datastore 240.

Figure 3:
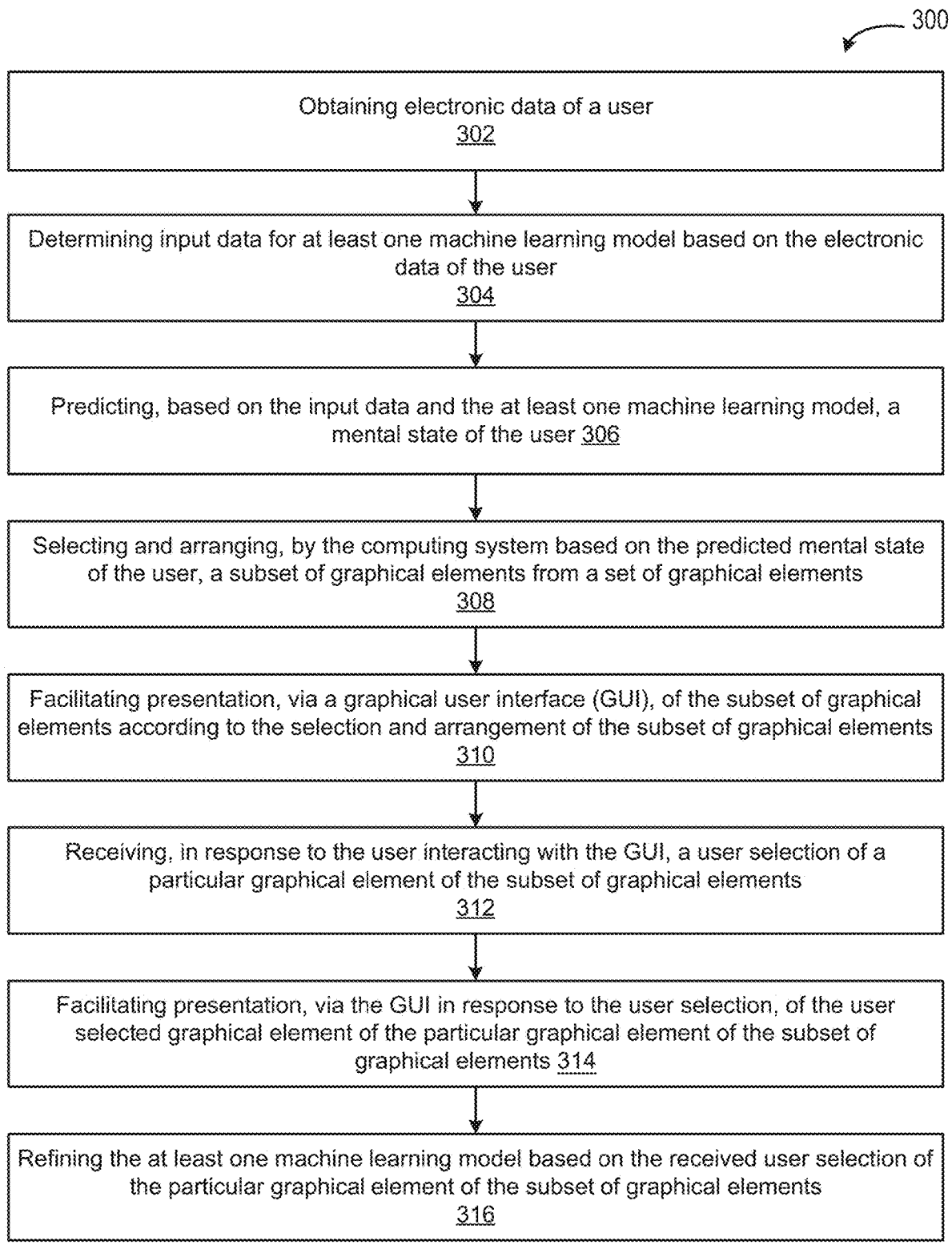
FIG. 3 depicts a flowchart of an example of a method of predicting mental state of a user using machine learning and selecting and arranging graphical elements based on the user's predicted mental state according to some embodiments.

FIG. 3 depicts a flowchart of an example of a method 300 of predicting mental state of a user using machine learning and selecting and arranging graphical elements based on the user's predicted mental state according to some embodiments. In this and other flowcharts and/or sequence diagrams, the flowchart illustrates by way of example a sequence of steps. It should be understood that some or all of the steps may be repeated, reorganized for parallel execution, and/or reordered, as applicable. Moreover, some steps that could have been included may have been removed to avoid providing too much information for the sake of clarity and some steps that were included could be removed, but may have been included for the sake of illustrative clarity.

In step 302, a machine learning-based state prediction and visualization system (e.g., machine learning-based state prediction and visualization system 102) obtains electronic data (e.g., electronic data 252) of a user (e.g., user system 104 and/or a user of a user system 104). In some embodiments, a communication engine (e.g., communication engine 220) and/or an electronic data collection engine (e.g., electronic data collection engine 208) obtains the electronic data over a communication network (e.g., communication network 108) from one or more user systems (e.g., user systems 104) and/or one or more third-party systems (e.g., third-party systems 106). A management engine (e.g., management engine 202) may store the electronic data in a datastore (e.g., machine learning-based state prediction and visualization system datastore 240).

In step 304, the machine learning-based state prediction and visualization system determines input data (e.g., machine learning input data 254) for at least one machine learning model (e.g., at least one machine learning model 256) based on the electronic data of the user. In some embodiments, a machine learning input data engine (e.g., machine learning input data engine 210) determines the input data.

In step 306, the machine learning-based state prediction and visualization system predicts, based on the input data and the at least one machine learning model (e.g., the input data may be provided as input to the machine learning model), a mental state of the user. The mental state may comprise a set of mood values (e.g., mood values 260), a set of uncertainty values, and a set of a magnitude values. Each mood value of the set of mood values may be associated with a corresponding uncertainty value of the set of uncertainty values and a corresponding magnitude value of the set of magnitude values. The magnitude value may indicate a relative strength and/or weakness of the associated mood value. In some embodiments, a machine learning-based state prediction engine (e.g., machine learning-based state prediction engine 212) performs the prediction. In some embodiments, the predicted mental state of the user (e.g., at a particular point of time and/or a particular period of time) may be stored by the management engine in a user profile (e.g., a user profile 250) and/or the datastore.

In step 308, the machine learning-based state prediction and visualization system selects and/or arranges, based on the predicted mental state of the user, a subset of graphical elements (e.g., graphical elements 258) from a set of graphical elements. For example, the graphical elements may be emojis. Each graphical element of the set of graphical elements may be associated (e.g., linked) with a corresponding mood value of the set of mood values. Each graphical element of the subset of graphical elements may be associated with the predicted mental state of the user. In some embodiments, a visualization engine (e.g., visualization engine 214) selects and/or arranges the graphical elements based on the mental state of the user (e.g., at one or more points of time and/or one or more periods of time).

In step 310, the machine learning-based state prediction and visualization system facilitates presentation (e.g., display), via a graphical user interface (GUI), of the subset of graphical elements according to the selection and arrangement of the subset of graphical elements. For example, the machine learning-based state prediction and visualization system may cause an associated device (e.g., a user system 104 of the user) to display the subset of graphical elements according to the selection and arrangement of the subset of graphical elements. In some embodiments, a presentation engine (e.g., presentation engine 218) and/or the visualization engine facilitates the presentation of the selection and arrangement of the graphical elements.

In step 312, the machine learning-based state prediction and visualization system receives, in response to the user interacting with the GUI presenting the subset of graphical elements according to the selection and arrangement of the subset of graphical elements, a user selection of a particular graphical element of the subset of graphical elements. For example, a user may select a particular graphical element displayed on their user system, and the selection may be communicated from the user system over the communication network to the communication engine, and the communication engine may then route the received selection to the presentation engine and/or the visualization engine. In some embodiments, the received selection may be used by a feedback engine (e.g., for example, 216) to refine, train, and/or otherwise improve the machine learning model and/or the machine learning-based state prediction engine.

In step 314, the machine learning-based state prediction and visualization system facilitates presentation (e.g., display), via the GUI in response to the user selection, of the user selection of the particular graphical element of the subset of graphical elements. In some embodiments, the presentation engine and/or visualization engine facilitates the presentation of the user selected graphical element.

In step 316, the machine learning-based state prediction and visualization system refines the at least one machine learning model based on the received user selection. In some embodiments, a feedback engine (e.g., feedback engine 216) refines the at least one machine learning model.

In some embodiments, step 312, like any of the other steps, may be optional. For example, step 314 may facilitate presentation of the particular graphical element in response to a user selection received at the user system (e.g., without the machine learning-based state prediction and visualization system receiving the user selection).

Figure 4:
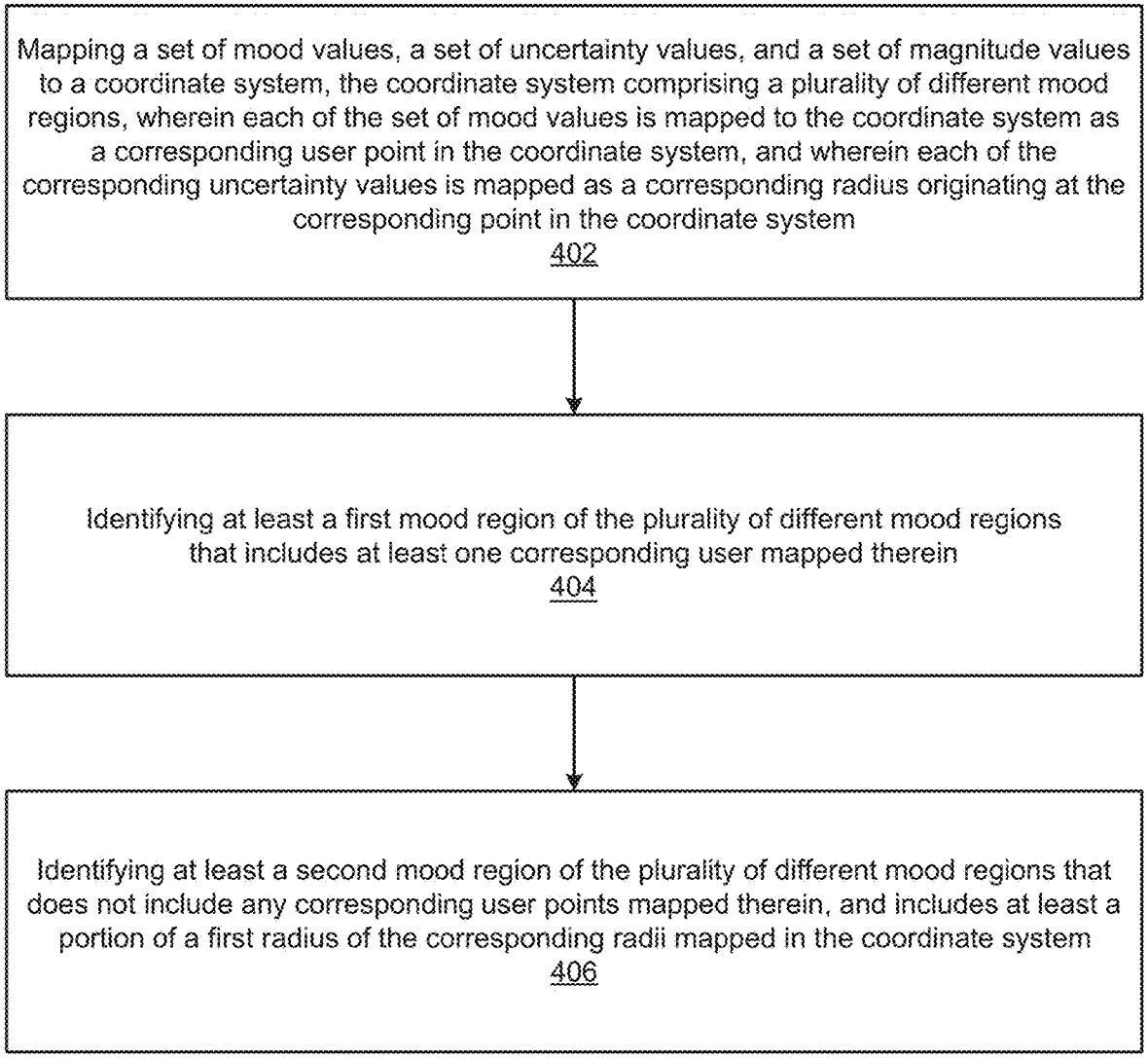
FIG. 4 depicts a flowchart of an example of a method of mental state prediction according to some embodiments.

FIG. 4 depicts a flowchart of an example of a method 400 of mental state prediction according to some embodiments. In this and other flowcharts and/or sequence diagrams, the flowchart illustrates by way of example a sequence of steps. It should be understood that some or all of the steps may be repeated, reorganized for parallel execution, and/or reordered, as applicable. Moreover, some steps that could have been included may have been removed to avoid providing too much information for the sake of clarity and some steps that were included could be removed, but may have been included for the sake of illustrative clarity.

In step 402, a machine learning-based state prediction and visualization system (e.g., machine learning-based state prediction and visualization system 102) maps a set of mood values (e.g., mood values 260), the set of uncertainty values, and the set of magnitude values to a coordinate system. The coordinate system may comprise a plurality of different mood regions. Each of the set of mood values may be mapped to the coordinate system as a corresponding user point in the coordinate system. Each of the corresponding uncertainty values may be mapped as a corresponding radius originating at the corresponding point in the coordinate system. In some embodiments, a machine learning-based state prediction engine (e.g., machine learning-based state prediction engine 212) and/or visualization engine 214 performs the mapping. In some embodiments, a mental state is defined by the mapping of step 402 (and/or other mappings described herein) and/or vice versa. Accordingly, in some instances, a user may have a unique mental state (e.g., different from any other user or previously known or defined mental state).

In step 404, the machine learning-based state prediction and visualization system identifies at least a first mood region of the plurality of different mood regions that includes at least one corresponding user mapped therein. In some embodiments, the machine learning-based state prediction engine and/or visualization engine performs the identification.

In step 406, the machine learning-based state prediction and visualization system identifies at least a second mood region of the plurality of different mood regions that does not include any corresponding user points mapped therein, and also includes at least a portion of a first radius of the corresponding radii mapped in the coordinate system. In some embodiments, the machine learning-based state prediction engine and/or visualization engine performs the identification.

In some embodiments, the mental state of the user is predicted based on the mood regions identified in steps 404 and 406, as well as the magnitude values associated with the at least one corresponding user point mapped in the at least a first mood region of the plurality of different moods regions and the first radius of the corresponding radii mapped in the coordinate system.

FIG. 5A depicts an example two-dimensional coordinate system 500 representing an example mental state according to some embodiments. The two-dimensional coordinate system 500 may be generated by the machine learning-based state prediction and visualization system 102. In some embodiments, the two-dimensional coordinate system 500 may be represented by one or more graphical user interfaces (e.g., generated by the machine learning-based state prediction and visualization system 102 and/or user systems 104).

As shown, the two-dimensional coordinate system 500 includes two-axes (e.g., the x-axis and the y-axis). The plotted points (e.g., first plotted point 510, second plotted point 520, and third plotted point 530) may represent respective moods at different times for an individual. For example, one individual may be associated with multiple points (e.g., first plotted point 512 and second plotted point 522) that each represent a particular mood at a particular point in time. The mental state may comprise the set of those plotted points. The points may be plotted in various mood regions of the two-dimensional coordinate system 500. For example, the mood regions may include a first mood region 502 (e.g., a happy mood region), a second mood region 504 (e.g., a sad mood region), a third mood region 506 (e.g., an angry mood region), and a fourth mood region 508. Each point may be associated with a magnitude value (e.g., 1.3 on a scale of 0.0 to 10.0, with 10.0 being the highest value indicating the strongest mood) and a radius indicating an uncertainty value associated with the plotted point. For example, a longer radius may indicate a higher uncertainty in the predicted mood and/or plotted point, and a short radius may indicate a lower uncertainty. In some examples, a plotted point may effectively overlap multiple mood regions based on the associated uncertainty value. For example, the second plotted point 520 has a magnitude value 522 of 9.5, and a radius 524 that extends into the second mood region.

FIG. 5B depicts an example three-dimensional coordinate system 550 representing an example mental state according to some embodiments. The three-dimensional coordinate system 550 may be generated by the machine learning-based state prediction and visualization system 102. In some embodiments, the three-dimensional coordinate system 550 may be represented by one or more graphical user interfaces (e.g., generated by the machine learning-based state prediction and visualization system 102 and/or user systems 104).

As shown, the three-dimensional coordinate system 550 includes three-axes (e.g., the x-axis, the y-axis, and the z-axis). The plotted points (e.g., first plotted point 560, second plotted point 570, and third plotted point 580) may represent respective moods at different times for an individual. For example, one individual may be associated with multiple points (e.g., first plotted point 562 and second plotted point 572) that each represent a particular mood at a particular point in time. The mental state may comprise the set of those plotted points associated with that individual. The points may be plotted in various mood regions of the three-dimensional coordinate system 550. For example, the mood regions may include a first mood region 552 (e.g., a happy mood region), a second mood region 554 (e.g., a sad mood region), a third mood region 556 (e.g., an angry mood region), and a fourth mood region 558. Each point may be associated with a magnitude value (e.g., 1.3 on a scale of 0.0 to 10.0, with 10.0 being the highest value indicating the strongest mood) and a radius indicating an uncertainty value associated with the plotted point. For example, a longer radius may indicate a higher uncertainty in the predicted mood and/or plotted point, and a short radius may indicate a lower uncertainty. In some examples, a plotted point may effectively overlap multiple mood regions based on the associated uncertainty value. For example, the second plotted point 570 has a magnitude value 572 of 9.5, and a radius 574 that extends into the second mood region.

It will be appreciated that the elements of the three-dimensional coordinate system 550 are represented with two-dimensional drawings for illustrative purposes. It will be appreciated that in some embodiments, each of the elements of FIG. 5B (e.g., mood regions, plotted points, radii, and/or the like) may be represented in three-dimensions instead of, or in addition to, two-dimensions.

Figure 6:
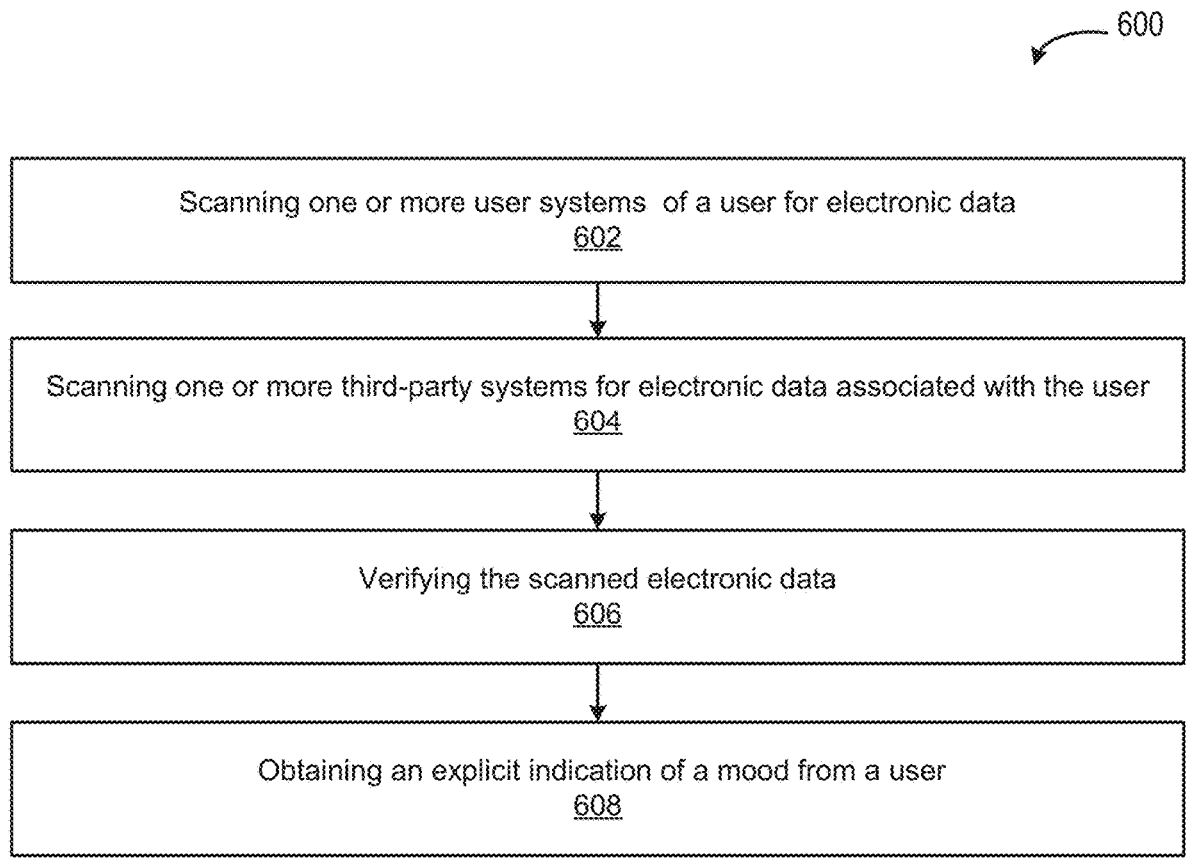
FIG. 6 depicts a flowchart of an example of a method of collecting electronic data of a user according to some embodiments.

FIG. 6 depicts a flowchart of an example of a method 600 of collecting electronic data of a user according to some embodiments. In this and other flowcharts and/or sequence diagrams, the flowchart illustrates by way of example a sequence of steps. It should be understood that some or all of the steps may be repeated, reorganized for parallel execution, and/or reordered, as applicable. Moreover, some steps that could have been included may have been removed to avoid providing too much information for the sake of clarity and some steps that were included could be removed, but may have been included for the sake of illustrative clarity.

In step 602, a machine learning-based state prediction and visualization system (e.g., machine learning-based state prediction and visualization system 102) scans one or more user systems (e.g., one or more user systems 104) of a user for electronic data (e.g., electronic data 252). In some embodiments, an electronic data collection engine (e.g., electronic data collection engine 208) performs the scan.

In step 604, the machine learning-based state prediction and visualization system scans one or more third-party systems (e.g., third-party systems 106) for electronic data associated with the user. For example, the machine learning-based state prediction and visualization system may scan social media accounts of the user for electronic data associated with the user. In some embodiments, the electronic data collection engine performs the scan.

In step 606, the machine learning-based state prediction and visualization system verifies whether the electronic data identified by the scans of step 602 and/or 604 may be used for mental state prediction of the user, and if so, verifies which electronic data may be used (e.g., certain data or all data). For example, the machine learning-based state prediction and visualization system may prompt the user for verification. In another example, the machine learning-based state prediction and visualization system may check the user's associated user profile (e.g., user profile 250) to determine verification. Verification may be performed before, during, or after a scan. In some embodiments, electronic data collection engine performs the verification(s).

In step 608, the machine learning-based state prediction and visualization system obtains an explicit indication of a mood from a user. For example, the machine learning-based state prediction and visualization system may prompt the user for their mood in response to a trigger event. In another example, a user may initiate providing an explicit indication of their mood to the machine learning-based state prediction and visualization system. In some embodiments, the electronic data collection engine obtains the explicit indication of mood from the user.

Figure 7:
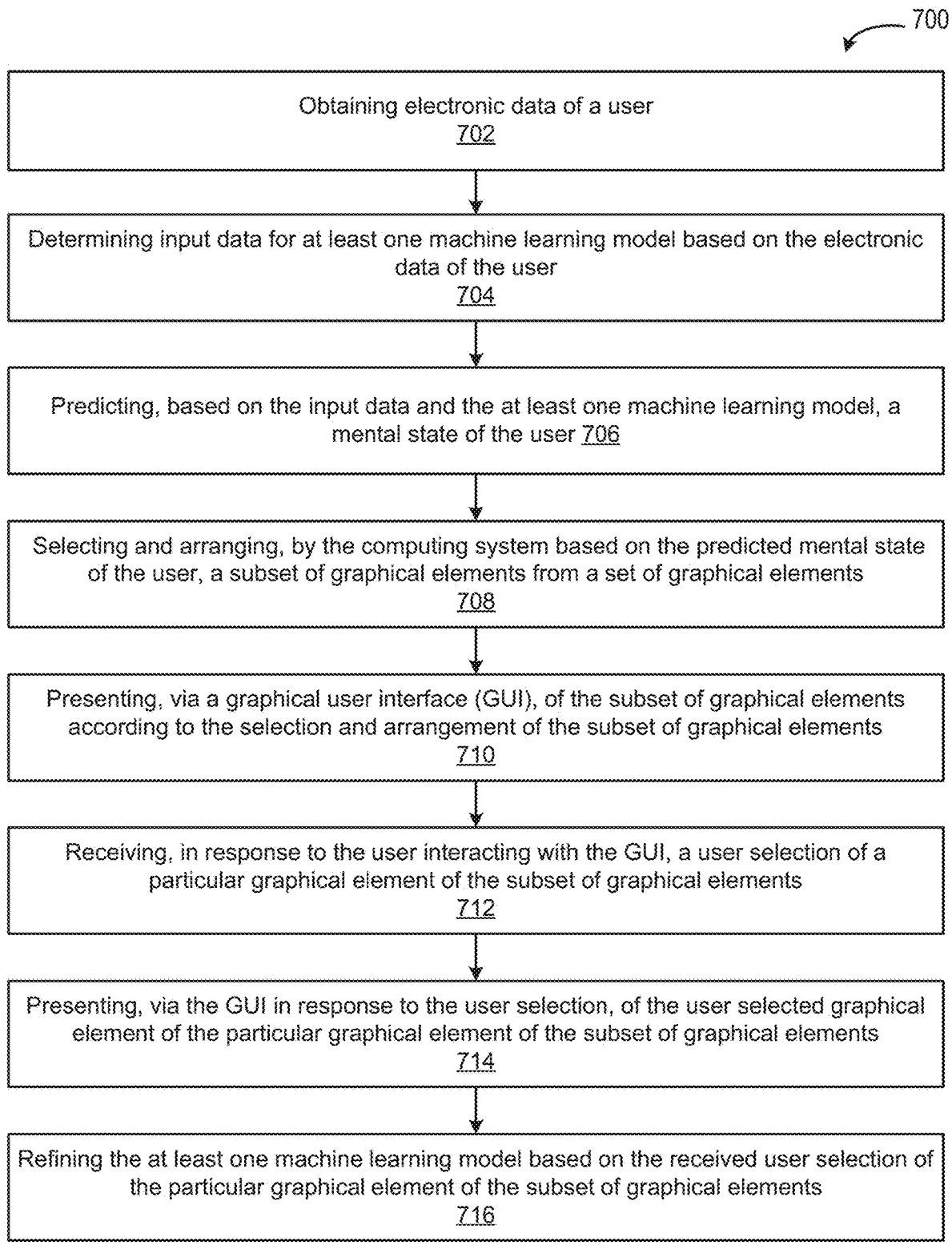
FIG. 7 depicts a flowchart of an example of a method of predicting mental state of a user using machine learning and selecting and arranging graphical elements based on the user's predicted mental state according to some embodiments.

FIG. 7 depicts a flowchart of an example of a method 700 of predicting mental state of a user using machine learning and selecting and arranging graphical elements based on the user's predicted mental state according to some embodiments. In this and other flowcharts and/or sequence diagrams, the flowchart illustrates by way of example a sequence of steps. It should be understood that some or all of the steps may be repeated, reorganized for parallel execution, and/or reordered, as applicable. Moreover, some steps that could have been included may have been removed to avoid providing too much information for the sake of clarity and some steps that were included could be removed, but may have been included for the sake of illustrative clarity.

In step 702, a machine learning-based state prediction and visualization system (e.g., machine learning-based state prediction and visualization system 102) obtains electronic data (e.g., electronic data 252) of a user (e.g., user system 104 and/or a user of a user system 104). In some embodiments, a communication engine (e.g., communication engine 220) and/or an electronic data collection engine (e.g., electronic data collection engine 208) obtains the electronic data over a communication network (e.g., communication network 108) from one or more user systems (e.g., user systems 104) and/or one or more third-party systems (e.g., third-party systems 106). A management engine (e.g., management engine 202) may store the electronic data in a datastore (e.g., machine learning-based state prediction and visualization system datastore 240).

In step 704, the machine learning-based state prediction and visualization system determines input data (e.g., machine learning input data 254) for at least one machine learning model (e.g., at least one machine learning model 256) based on the electronic data of the user. In some embodiments, a machine learning input data engine (e.g., machine learning input data engine 210) determines the input data.

In step 706, the machine learning-based state prediction and visualization system predicts, based on the input data and the at least one machine learning model, a mental state of the user. The mental state may comprise a set of mood values (e.g., mood values 260), a set of uncertainty values, and a set of a magnitude values. Each mood value of the set of mood values may be associated with a corresponding uncertainty value of the set of uncertainty values and a corresponding magnitude value of the set of magnitude values. The magnitude value may indicate a relative strength and/or weakness of the associated mood value. In some embodiments, a machine learning-based state prediction engine (e.g., machine learning-based state prediction engine 212) performs the prediction. In some embodiments, the predicted mental state of the user (e.g., at a particular point of time and/or a particular period of time) may be stored by the management engine in a user profile (e.g., a user profile 250) and/or the datastore.

In step 708, the machine learning-based state prediction and visualization system selects and/or arranges, based on the predicted mental state of the user, a subset of graphical elements (e.g., graphical elements 258) from a set of graphical elements. For example, the graphical elements may be emojis. Although method 700 uses graphical elements, it will be appreciated that the method 700 may also use other types of elements (e.g., other types of emotional indicators) instead of, or in addition to, graphical elements. Each graphical element of the set of graphical elements may be associated (e.g., linked) with a corresponding mood value of the set of mood values. Each graphical element of the subset of graphical elements may be associated with the predicted mental state of the user. In some embodiments, a visualization engine (e.g., visualization engine 214) selects and/or arranges the graphical elements based on the mental state of the user (e.g., at one or more points of time and/or one or more periods of time).

In step 710, the machine learning-based state prediction and visualization system presents (e.g., displays), via a graphical user interface (GUI), the subset of graphical elements according to the selection and arrangement of the subset of graphical elements. For example, the machine learning-based state prediction and visualization system may cause an associated device (e.g., a user system 104 of the user) to display the subset of graphical elements according to the selection and arrangement of the subset of graphical elements. In some embodiments, a presentation engine (e.g., presentation engine 218) and/or the visualization engine facilitates the presentation of the selection and arrangement of the graphical elements.

In step 712, the machine learning-based state prediction and visualization system receives, in response to the user interacting with the GUI presenting the subset of graphical elements according to the selection and arrangement of the subset of graphical elements, a user selection of a particular graphical element of the subset of graphical elements. For example, a user may select a particular graphical element displayed on their user system, and the selection may be communicated from the user system over the communication network to the communication engine, and the communication engine may then route the received selection to the presentation engine and/or the visualization engine. In some embodiments, the received selection may be used by a feedback engine (e.g., for example, 216) to refine, train, and/or otherwise improve the machine learning model and/or the machine learning-based state prediction engine.

In step 714, the machine learning-based state prediction and visualization system presents (e.g., displays), via the GUI in response to the user selection, the user selected graphical element of the particular graphical element of the subset of graphical elements. In some embodiments, the presentation engine and/or visualization engine facilitates the presentation of the user selected graphical element.

In step 716, the machine learning-based state prediction and visualization system refines the at least one machine learning model based on the received user selection. In some embodiments, a feedback engine (e.g., feedback engine 216) refines the at least one machine learning model.

In some embodiments, step 712, like any of the other steps, may be optional. For example, step 714 may present the particular graphical element in response to a user selection received at the user system (e.g., without the machine learning-based state prediction and visualization system receiving the user selection).

Figure 8:
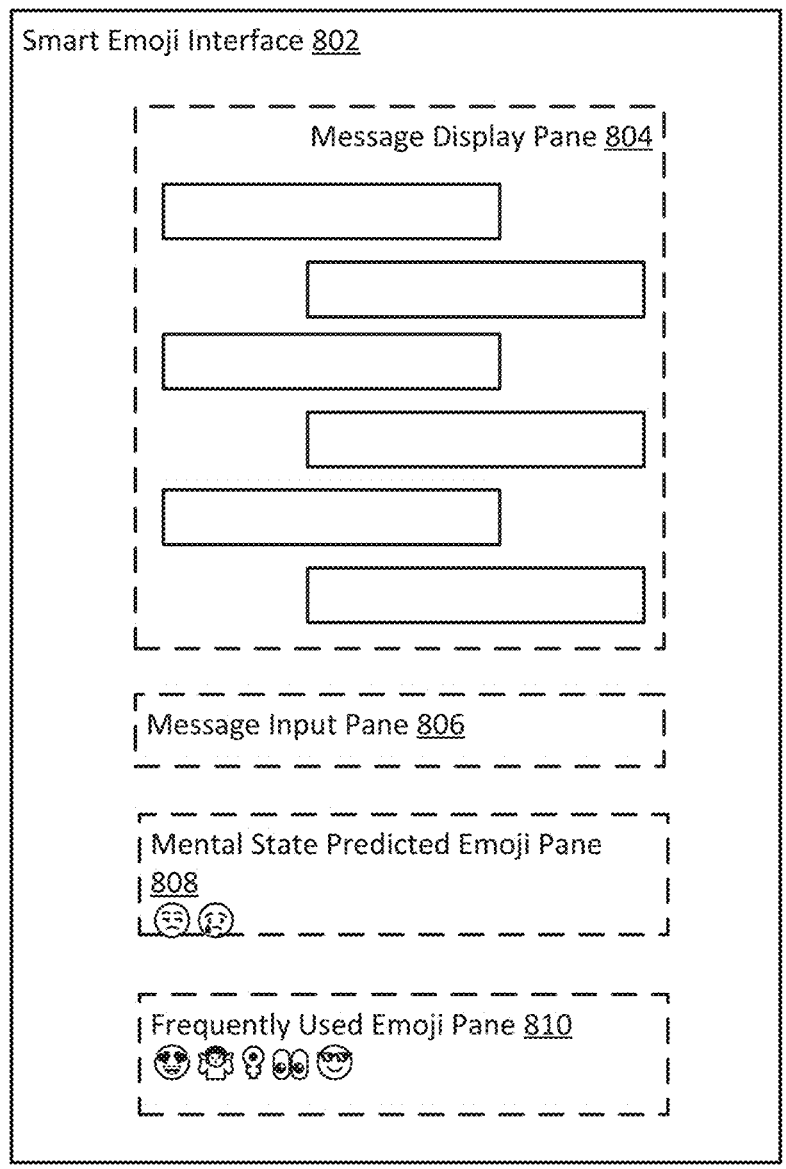
FIG. 8 depicts an example graphical user interface with graphical elements selected and arranged using machine learning-based state prediction according to some embodiments.

FIG. 8 depicts an example graphical user interface (or, smart emoji interface) 802 with graphical elements selected and arranged using machine learning-based state prediction according to some embodiments. In the example of FIG. 8, the graphical user interface 802 includes a message display pane 804, a message input pane 806, a mental state predicted emoji pane 808, and a frequently used emoji pane 810.

In some embodiments, the graphical user interface 802 is an example of the type of interface that may be generated, or at least partially generated, by a machine learning-based state prediction and visualization system 102. For example, the machine learning-based state prediction and visualization system 102 may predict a mental state of a user associated with a user system 104 which presents the graphical user interface 802. In this example, the user is predicted to have a mental state that is associated with an angry emoji and a sad emoji. Accordingly, the angry emoji and the sad emoji are presented in the mental state predicted emoji pane 808. Notably, these are different emojis than the frequently used emojis presented in the frequently used emoji pane 810.

It will be appreciated that the graphical user interface 802 is presented merely by way of example, and that other interfaces generated, or partially generated, by the machine learning-based state prediction and visualization system 102 may different. For example, other interfaces may have elements 804-810 arranged differently, some elements may be removed (e.g., the frequently used emoji pane 810), other elements may be added (e.g., a scrollable list of all available emojis), some elements may be combined (e.g., panes 808 and 810), and/or the like.

Figure 9:
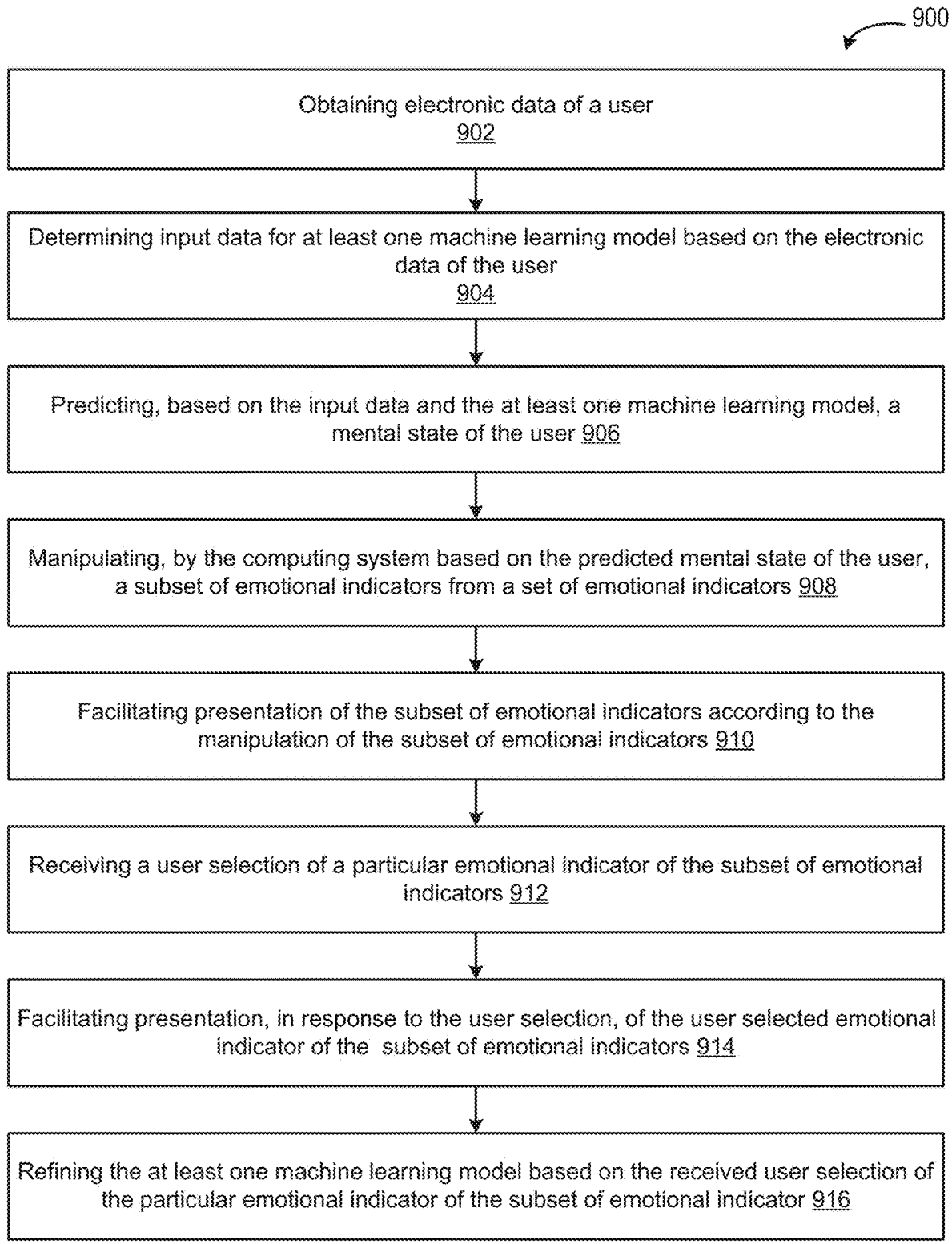
FIG. 9 depicts a flowchart of an example of a method of predicting mental state of a user using machine learning and manipulating (e.g., selecting and arranging) graphical elements based on the user's predicted mental state according to some embodiments.

FIG. 9 depicts a flowchart of an example of a method 900 of predicting mental state of a user using machine learning and manipulating (e.g., selecting and arranging) emotional indicators based on the user's predicted mental state according to some embodiments. In this and other flowcharts and/or sequence diagrams, the flowchart illustrates by way of example a sequence of steps. It should be understood that some or all of the steps may be repeated, reorganized for parallel execution, and/or reordered, as applicable. Moreover, some steps that could have been included may have been removed to avoid providing too much information for the sake of clarity and some steps that were included could be removed, but may have been included for the sake of illustrative clarity.

In step 902, a machine learning-based state prediction and visualization system (e.g., machine learning-based state prediction and visualization system 102) obtains electronic data (e.g., electronic data 252) of a user (e.g., user system 104 and/or a user of a user system 104). In some embodiments, a communication engine (e.g., communication engine 220) and/or an electronic data collection engine (e.g., electronic data collection engine 208) obtains the electronic data over a communication network (e.g., communication network 108) from one or more user systems (e.g., user systems 104) and/or one or more third-party systems (e.g., third-party systems 106). A management engine (e.g., management engine 202) may store the electronic data in a datastore (e.g., machine learning-based state prediction and visualization system datastore 240).

In step 904, the machine learning-based state prediction and visualization system determines input data (e.g., machine learning input data 254) for at least one machine learning model (e.g., at least one machine learning model 256) based on the electronic data of the user. In some embodiments, a machine learning input data engine (e.g., machine learning input data engine 210) determines the input data.

In step 906, the machine learning-based state prediction and visualization system predicts, based on the input data and the at least one machine learning model, a mental state of the user. The mental state may comprise a set of mood values (e.g., mood values 260), a set of uncertainty values, and a set of a magnitude values. Each mood value of the set of mood values may be associated with a corresponding uncertainty value of the set of uncertainty values and a corresponding magnitude value of the set of magnitude values. The magnitude value may indicate a relative strength and/or weakness of the associated mood value. In some embodiments, a machine learning-based state prediction engine (e.g., machine learning-based state prediction engine 212) performs the prediction. In some embodiments, the predicted mental state of the user (e.g., at a particular point of time and/or a particular period of time) may be stored by the management engine in a user profile (e.g., a user profile 250) and/or the datastore.

In step 908, the machine learning-based state prediction and visualization system manipulates (e.g., selects and/or arranges), based on the predicted mental state of the user, a subset of emotional indicators (e.g., graphical elements 258) from a set of emotional indicators. For example, the emotional indicators may be graphical elements (e.g., emojis), audio elements, haptic elements, and/or the like. Each emotional indicator of the set of emotional indicators may be associated (e.g., linked) with a corresponding mood value of the set of mood values. Each emotional indicator of the subset of emotional indicators may be associated with the predicted mental state of the user. In some embodiments, a visualization engine (e.g., visualization engine 214) manipulates the emotional indicators based on the mental state of the user (e.g., at one or more points of time and/or one or more periods of time).

In step 910, the machine learning-based state prediction and visualization system facilitates presentation (e.g., display), via a graphical user interface (GUI), of the subset of emotional indicators according to the manipulation of the subset of emotional indicators. For example, the machine learning-based state prediction and visualization system may cause an associated device (e.g., a user system 104 of the user) to present (e.g., display) the subset of emotional indicators according to the manipulation of the subset of emotional indicators. In some embodiments, a presentation engine (e.g., presentation engine 218) and/or the visualization engine facilitates the presentation of the manipulation of the emotional indicators.

In step 912, the machine learning-based state prediction and visualization system receives, in response to the user interacting with the GUI presenting the subset of emotional indicator according to the manipulation of the subset of emotional indicator, a user selection of a particular emotional indicator of the subset of emotional indicator. For example, a user may select a particular emotional indicator presented on their user system, and the selection may be communicated from the user system over the communication network to the communication engine, and the communication engine may then route the received selection to the presentation engine and/or the visualization engine. In some embodiments, the received selection may be used by a feedback engine (e.g., for example, 216) to refine, train, and/or otherwise improve the machine learning model and/or the machine learning-based state prediction engine.

In step 914, the machine learning-based state prediction and visualization system facilitates presentation (e.g., display), in response to the user selection (e.g., via the GUI), of the user selection of the particular emotional indicator of the subset of emotional indicators. In some embodiments, the presentation engine and/or visualization engine facilitates the presentation of the user selected emotional indicator.

In step 916, the machine learning-based state prediction and visualization system refines the at least one machine learning model based on the received user selection. In some embodiments, a feedback engine (e.g., feedback engine 216) refines the at least one machine learning model.

In some embodiments, step 912, like any of the other steps, may be optional. For example, step 914 may facilitate presentation of the particular emotional indicator in response to a user selection received at the user system (e.g., without the machine learning-based state prediction and visualization system receiving the user selection).

Figure 10:
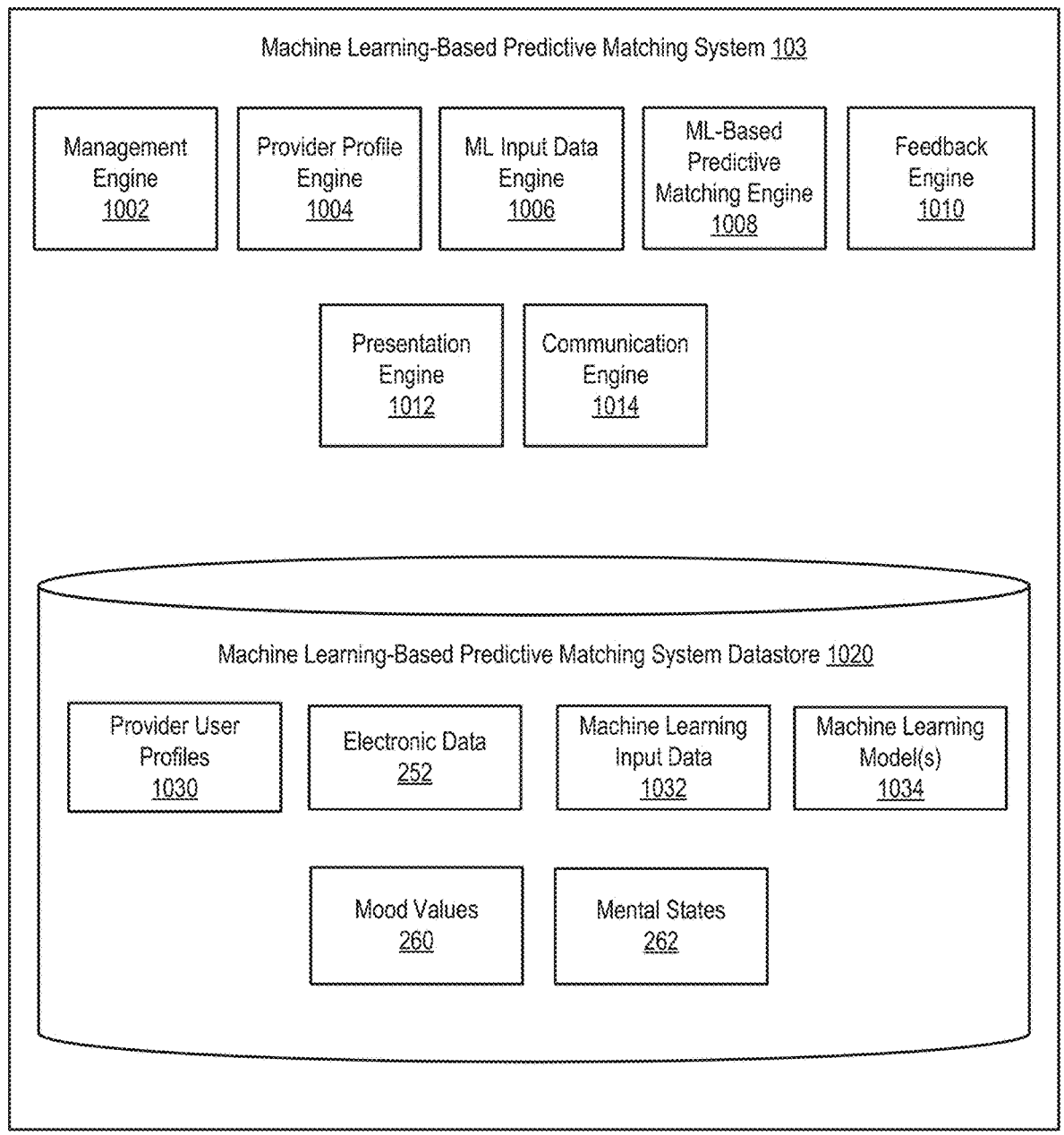
FIG. 10 depicts an example machine learning-based predictive matching system according to some embodiments.

FIG. 10 depicts an example machine learning-based predictive matching system 103 according to some embodiments. In the example of FIG. 10, the machine learning-based predictive matching system 103 includes a management engine 1002, a provider profile engine 1004, a machine learning input data engine 1006, a machine learning-based predictive matching engine 1008, a feedback engine 1010, a presentation engine 1012, a communication engine 1014, and a machine learning-based predictive matching system datastore 1020.

The management engine 1002 may function to manage (e.g., create, read, update, delete, or otherwise access) provider user profiles 1030, electronic data 252, machine learning input data 1032, machine learning model(s) 1034, mood values 260 (or, simply, "moods"), and/or mental states 262. The management engine 1002 can perform any of these operations manually (e.g., by a user interacting with a GUI) and/or automatically (e.g., triggered by one or more of the engines 1004-1014). Like the other engines described herein, some or all the functionality of the management engine 1002 can be included in and/or cooperate with one or more other engines (e.g., engines 1004-1014) and datastores (e.g., machine learning-based predictive matching system datastore 1020).

The provider profile engine 1004 may function to register provider users (e.g., medical provider or other service provider), register associated user systems 104 (e.g., a mobile device of the provider user), register user accounts (e.g., the provider user's accounts of third-party systems 106), and/or generate provider user profiles 1030. Provider user profiles 1030 may include some or all of the following information:

- Provider User Profile Identifier: identifies the provider user profile.
- Provider User Identifier: identifies the provider user.
- Provider User Credentials: username, password, two-factor authentication, and/or other credentials.
- Provider User Personal Information: identifies the provider user's name, contact information (e.g., email address, phone number, mailing address).
- Registered (or, associated) User Systems: Identifies user systems 104 associated with the provider user.
- Registered (or, associated) Accounts and/or Third-Party Systems: identifies provider user accounts (e.g., social media accounts), and associated access information (e.g., APIs, user account names and credentials, and/or the like).
- Mood History: History of identified moods for the user and associated time stamps.
- Mental State History: history of mental states predicted by the machine learning-based state prediction and visualization system for the user, and associated timestamps.
- Current Mental State: a current mental state of the user predicted by the machine learning-based state prediction and visualization system.
- User Privacy Settings: identifies which electronic data 250, or types of electronic data (e.g., text messages), may be used for predicting mental state.
- Electronic data: electronic data 252 obtained by the machine learning-based state prediction and visualization system 102, and/or references (e.g., pointers, links) to electronic data 252 obtained by the machine learning-based state prediction and visualization system.
- Goals (or, Criteria): Goals and/or criteria of the provider.

In various embodiments, the provider user profiles 1030 may be used by some or all of the engines described herein to perform their functionality described herein.

The machine learning input data engine 1006 may function to generate input data 1032 for one or machine learning models 1034 (e.g., machine learning models of the machine learning-based predictive matching engine 1008). The machine learning models 1034 may comprise machine learning models for predicting matches (e.g., therapeutic matches). The machine learning input data engine 1006 may generate the machine learning input data 1032 based on some or all of the electronic data 252. For example, the machine learning input data engine 1006 may generate machine learning input data 1032 based on some or all of the electronic data 252 associated with a particular user (e.g., user John Smith). In some embodiments, the machine learning input data engine 1006 may normalize the electronic data 252 to a normalized data format, and the normalized data format may comprise the data format of the machine learning input data 1032. This may allow, for example, the machine learning-based predictive matching system 103 to obtain data from a variety of different sources regardless of their original format and allow the machine learning-based predictive matching system 103 to operate on the data regardless of the original format.

In some embodiments, the machine learning input data engine 1006 generates the machine learning input data 1032 based on predicted mental states (e.g., predicted mental state of a patient user, predicted mental states of provider users), one or more inventories of preferences of a user (e.g., C-NIP, URICA) and/or inventory scores, one or more goals or criteria of a user (e.g., a patient users), one or more goals of other users (e.g., provider users), and/or labeled session data associated with a plurality of successful therapeutic matches. In some embodiments, the machine learning input data engine 1006 may normalize some or all of the aforementioned data (e.g., inventory of preferences data) to a normalized data format, and the normalized data format may comprise the data format of the machine learning input data 1032. This may allow, for example, the machine learning-based predictive matching system 103 to obtain data from a variety of different sources regardless of their original format and allow the machine learning-based predictive matching system 103 to operate on the data regardless of the original format.

The labeled session data may comprise data from previous therapy sessions (e.g., early-stage therapy sessions) that have been labeled as successful and/or unsuccessful. For example, the session data may be labeled based on whether a patient user and/or a provider user indicated that the session(s) were successful. The session data may include data of the patient user, provider user, associated inventories of preferences, associated goals and/or criteria, associated match predictions, associated mental state predictions, and/or other associated data described herein. Early-stage therapy sessions may include therapy sessions between a first session and a firth session, for example.

The machine learning-based predictive matching engine 1008 may function to predict matches between users (e.g., patient users and provider users) based on one or more predicted mental states of one or more users (e.g., patient user and provider users) using one or more machine learning models 1034. The machine learning models 1034 may include Bayesian machine learning models and/or other type of machine learning model described herein. In some embodiments, the machine learning-based predictive matching engine 1008 may predict a therapeutic match or a therapeutic alliance between a user (e.g., a patient user) and a provider user from a set of different provider users.

In some embodiments, the machine learning-based predictive matching engine 1008 predicts a match (e.g., therapeutic match) and/or an alliance (e.g., therapeutic alliance) between one or more users (e.g., a patient user) and one or more other users (e.g., provider users) from a set of different users (e.g., set of different provider users). As used herein, an alliance can be a cooperative working relationship between users (e.g., between a patient user and a provider user) and/or an indication thereof. It will be appreciated that reference to a "match" herein can include and/or consist of one or more alliances. In some embodiments, an alliance comprises one or more alliance parameters. The alliance parameters can include agreement (e.g., between users) of goals (e.g., treatment goals), agreement on tasks, and development of a personal bond comprising reciprocal positive feelings. The machine learning-based predictive matching engine 1008 may predict a match if an alliance score (e.g., a score based on some or all of the alliance parameters) satisfies an alliance threshold. For example, the machine learning-based predictive matching engine 1008 may predict a match between users if an output of a machine learning model 1034 satisfies the alliance threshold (e.g., meets or exceeds the alliance threshold). In some embodiments, the machine learning-based predictive matching engine 1008 can predict unsuccessful matches as well as successful matches. For example, an unsuccessful match may comprise an alliance score that does not satisfy the alliance threshold (e.g., the output of the machine learning model 1034 is below the alliance threshold score).

In some embodiments, a match prediction (or alliance prediction) is based on a connection score determined by the machine learning-based predictive matching engine 1008 and an efficacy (e.g., therapeutic efficacy or other service efficacy) score determined by the machine learning-based predictive matching engine 1008, as discussed elsewhere herein. A connection score can indicate a personal connector and/or a sense of belong a user has, or predicted to have, with a provider user. The efficacy score can indicate a score related to other factors, such as the likelihood that goals or criteria will be met.

In some embodiments, the machine learning-based predictive matching engine 1008 determines and/or obtains one or more inventories of preferences of the first user. For example, the inventories of preferences can include the Cooper-Norcross Inventory of Preferences (C-NIP), the University of Rhode Island Change Assessment Score (URICA), and/or the like. Determining the one or more inventories can include determining questions of the one or more inventories, determining answers to the one or questions (e.g., in response to first user input), and/or determining an inventory score (e.g., between 1 and 100) based on the inventory questions, the inventory answers, and/or one or more parameters of the inventory. The inventory score can be calculated by the machine learning-based predictive matching engine 1008 based on one or more parameters of the inventories. For example, the one or more parameters of the inventories can include a default calculation formula, weighted values, models, and/or the like. In some embodiments, the machine learning-based predictive matching engine 1008 may calculate a tuned inventory score based on an adjustment of one or more parameters of the inventories of preferences (e.g., based on mental state of a user), as discussed elsewhere herein.

In some embodiments, an inventory of preferences can include one or more goals or criteria of service (e.g., therapy goals or requirements) of a user (e.g., a patient user). For example, the one or more goals may include a desired therapy (e.g., CBT therapy), a desired geographic location of therapy, a desired gender of provider, a desired demographic of the provider (e.g., gender, race, income, and/or the like), and/or other criteria pertaining to the therapy and/or the provider.

In some embodiments, the machine learning-based predictive matching engine 1008 determines one or more respective goals for each second user of the plurality of second users. For example, the goals (e.g., criteria) can include type of therapy (e.g., CBT therapy), a desired geographic location of therapy, a desired demographic of patient (e.g., gender, race, income, and/or the like) of provider, and/or other criteria pertaining to the therapy and/or the provider.

In some embodiments, the machine learning-based predictive matching engine 1008 generates (e.g., builds from scratch and/or builds from a template machine learning model, and/or refines a live machine learning model and/or refines a template machine learning model) one or more machine learning models (e.g., machine learning models 1034) based on the mental state of the a user (e.g., patient user), the mental state(s) of each of the plurality of other users (e.g., provider users), the inventories of preferences of the user, the one or more respective goals of the user and the other users, and/or the labeled session data.

In some embodiments, the machine learning-based predictive matching engine 1008 predicts, based on a mental state of a user (e.g., patient user), the mental states of a plurality of other users (e.g., provider users), the inventories of preferences of the user, the labeled session data, and/or one or more machine learning models, one or more matches (e.g., therapeutic matches) between the user and the other users. For example, the mental state of the user, the mental states of the other users, the inventories of preferences of the user (e.g., an inventory score calculated using a default inventory calculation formula and/or a tuned inventory score calculated using a tuned inventory calculation formula), and/or the labeled session data may be provided as input to the one or more machine learning models and the output can indicate whether there is a match between the user and one or more of the other users.

In some embodiments, the machine learning-based predictive matching engine 1008 automatically connects, in response to receiving the user selection of the particular second user of the one or more second users of the plurality of second users, the first user with each of the one or more second users of the plurality of second users. For example, the machine learning-based predictive matching engine 1008 may connect the users via electronic mail, social media, telephone, text message, mobile application, and/or the like. For example, the machine learning-based predictive matching engine 1008 may trigger a notification on a matched user's device (e.g., patient user device, provider user device). In some embodiments, the device may be triggered even if the notification is sent while the device is offline (e.g., asleep, without network access, turned off). For example, the notification may be triggered when the device wakes up, access a network, or is turned on. In some embodiments, the notification may trigger the device to wake up, access a network, and/or turn on.

In some embodiments, the machine learning-based predictive matching engine 1008 generates, based on the one or more machine learning models and the provided machine learning input data, a respective connection score for each of one or more user pairs. As used herein, a user pair is a first user (e.g., a patient user) and another user (e.g., provider user) of a set of different users (e.g., a set of provider users). For example, if there is as patient user and ten provider users, there would be ten different user pairs. The connection score may be an output of the one or more machine learning models (e.g., a first machine learning model of the one or more machine learning models) and/or based on the output.

In some embodiments, the machine learning-based predictive matching engine 1008 generates, based on the one or more machine learning models and the provided machine learning input data, a respective efficacy score for each of one or more user pairs. The efficacy score may be an output of the one or more machine learning models (e.g., a second machine learning model of the one or more machine learning models) and/or based on the output. In some embodiments, the machine learning-based predictive matching engine 1008 generates, based on the respective connection scores and the respective efficacy scores, a respective alliance (or, match) score for each user pair.

In some embodiments, the machine learning-based predictive matching engine 1008 can plot, and/or otherwise include, the connection scores and efficacy as part of a multi-dimensional axis and/or coordinate system. For example, connection scores may correspond to a first axis of the multi-dimensional axis and/or coordinate system, and the efficacy scores may correspond to a second axis of the multi-dimensional axis and/or coordinate system.

In some embodiments, the machine learning-based predictive matching engine 1008 compares each of the respective alliances scores with a threshold alliance score. The machine learning-based predictive matching engine 1008 can predict, based on the comparisons, for each user whether the pair is a predicted successful match and/or a predicted unsuccessful match. For example, if an alliance score satisfies the threshold alliance score (e.g., it meets or exceeds the alliance threshold score), then the machine learning-based predictive matching system may predict a successful match, and if an alliance score does not satisfy the threshold alliance score (e.g., it is below the alliance threshold score), then the machine learning-based predictive matching system may predict an unsuccessful match.

The feedback engine 1010 may function to train, refine, and/or otherwise improve the machine learning and/or machine learning models 1034 described herein. In some embodiments, the feedback engine 216 receives user selections of provider users for a set of predicted successful matches. In some embodiments, the user selections may occur after a provider has been selected, and the user may indicate whether the predicted successful match was an actual successful match (e.g., according to input received from the patient user and/or provider user). The feedback engine 216 may utilize the user selections to adjust parameters of the machine learning models 1034, and/or otherwise train, retrain, refine, and/or improve the corresponding machine learning and/or machine learning models 1034.

The presentation engine 1012 may function to present visual, audio, and/or haptic information. In some embodiments, the presentation engine 1012 generates graphical user interfaces, and/or components thereof (e.g., server-side graphical user interface components) that can be rendered as complete graphical user interfaces on remote systems (e.g., user systems 104). In some embodiments, the presentation engine 1202 receives and/or transmits data. For example, the presentation engine can receive and/or transmit user selections (e.g., received through a graphical interface generated by the presentation engine 1012.

The communication engine 1014 may function to send requests, transmit and receive communications, and/or otherwise provide communication with one or more of the systems, engines, devices and/or datastores described herein. In a specific implementation, the communication engine 1014 may function to encrypt and decrypt communications. The communication engine 1014 may function to send requests to and receive data from one or more systems through a network or a portion of a network (e.g., communication network 108). In a specific implementation, the communication engine 1014 may send requests and receive data through a connection, all or a portion of which can be a wireless connection. The communication engine 1014 may request and receive messages, and/or other communications from associated systems and/or engines. Communications may be stored in the machine learning-based predictive matching system datastore 1020.

Figure 11A:
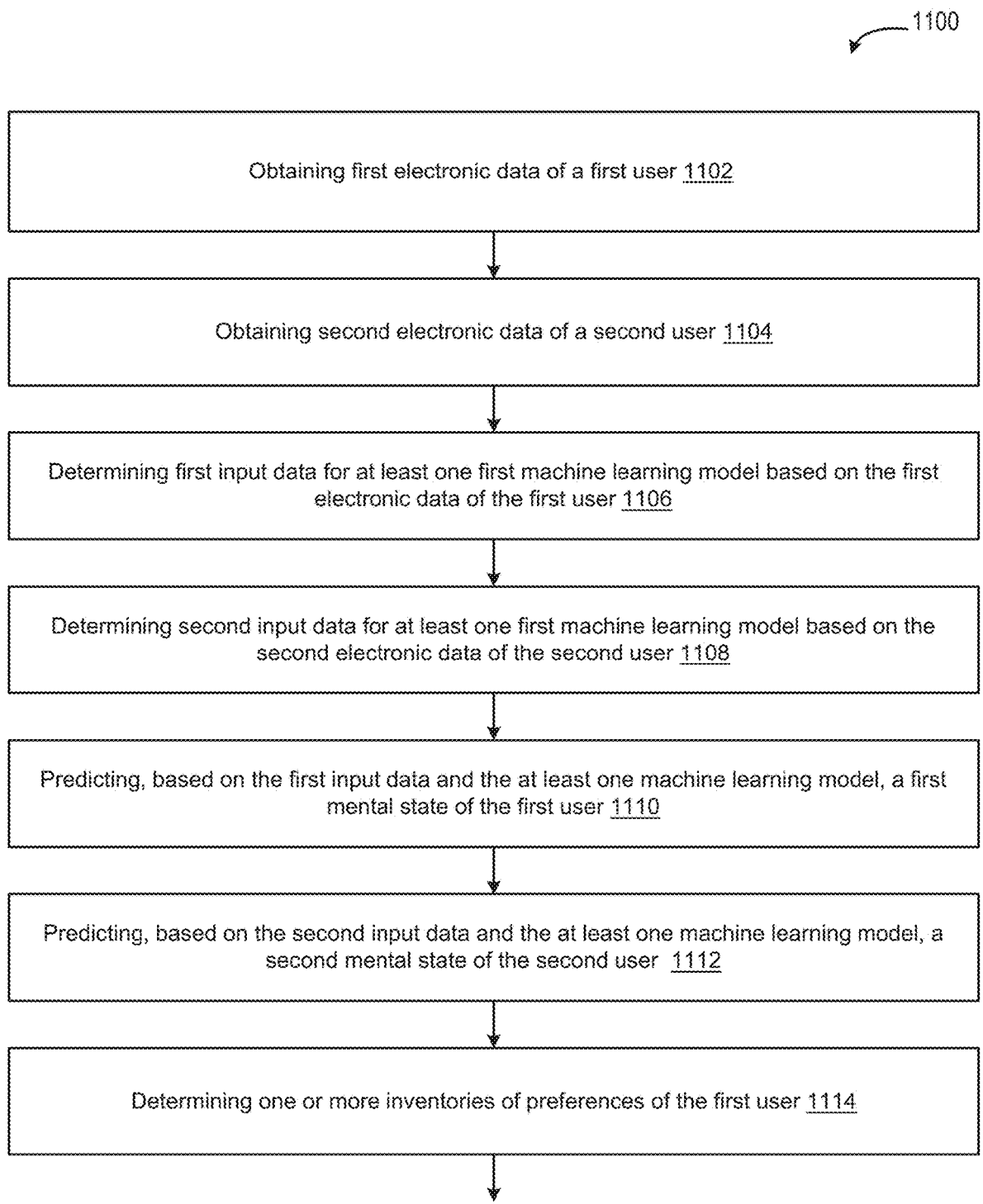
FIGS. 11A-B depict a flowchart of an example of a method of machine learning-based match prediction according to some embodiments.
Figure 11B:
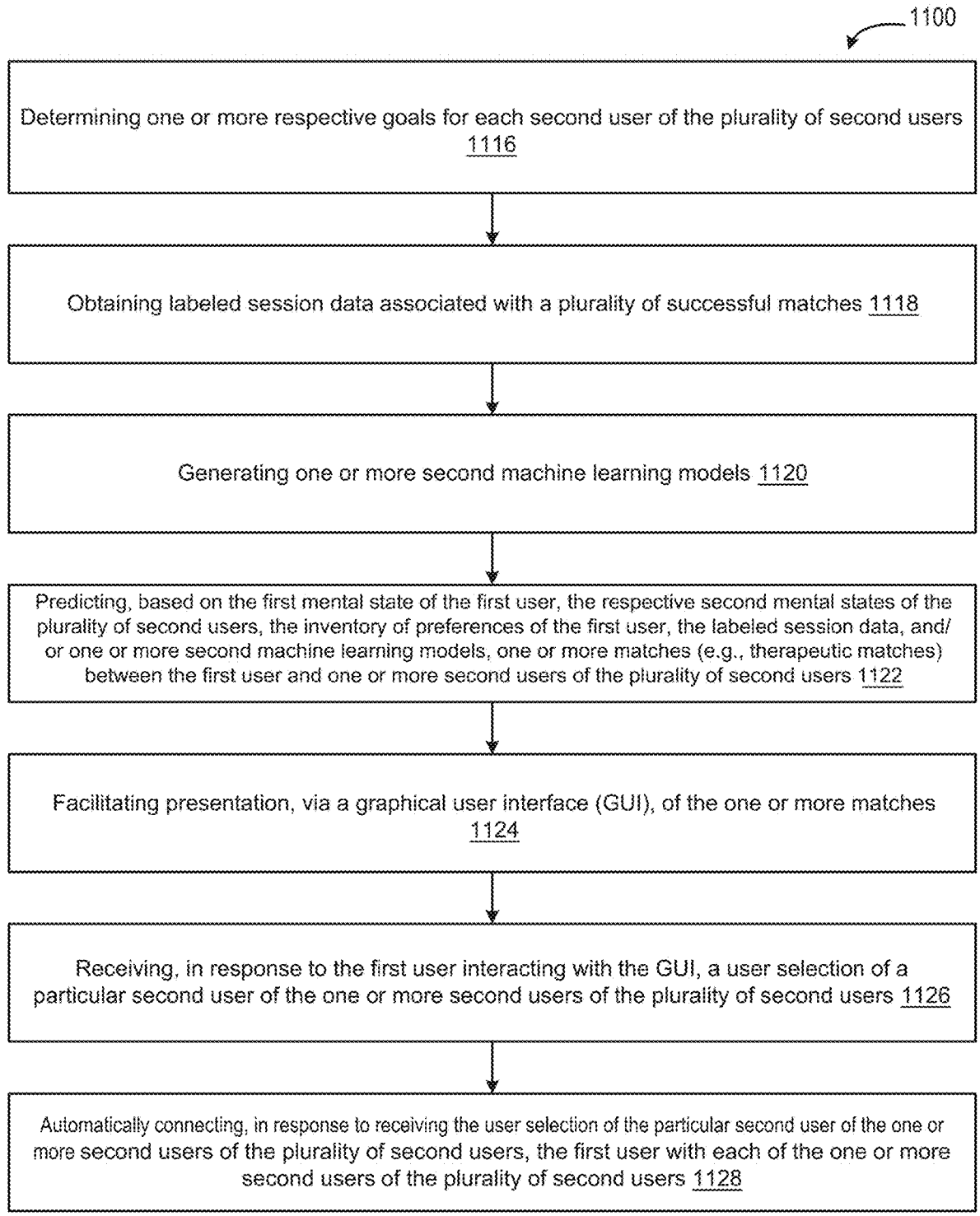

FIGS. 11A-B depict a flowchart of an example of a method 1100 of machine learning-based match (e.g., therapeutic match) prediction according to some embodiments. In this and other flowcharts and/or sequence diagrams, the flowchart illustrates by way of example a sequence of steps. It should be understood that some or all of the steps may be repeated, reorganized for parallel execution, and/or reordered, as applicable. Moreover, some steps that could have been included may have been removed to avoid providing too much information for the sake of clarity and some steps that were included could be removed, but may have been included for the sake of illustrative clarity.

In step 1102, a machine learning-based state prediction and visualization system (e.g., machine learning-based state prediction and visualization system 102) obtains first electronic data (e.g., electronic data 252) of a first user (e.g., user system 104 and/or a patient user of a user system 104). In some embodiments, a communication engine (e.g., communication engine 220) and/or an electronic data collection engine (e.g., electronic data collection engine 208) obtains the first electronic data over a communication network (e.g., communication network 108) from one or more user systems (e.g., user systems 104) and/or one or more third-party systems (e.g., third-party systems 106). A management engine (e.g., management engine 202) may store the first electronic data in one or more datastores (e.g., machine learning-based state prediction and visualization system datastore 240 and/or machine learning-based predictive matching system datastore 1020).

In step 1104, the machine learning-based state prediction and visualization system obtains second electronic data (e.g., electronic data 252) for each of a plurality of second users (e.g., user systems 104 and/or provider users of the user systems 104). In some embodiments, the communication engine and/or the electronic data collection engine obtains the second electronic data over the communication network from one or more user systems (e.g., user systems 104) and/or one or more third-party systems (e.g., third-party systems 106). The management engine may store the second electronic data in the one or more datastores.

In step 1106, the machine learning-based state prediction and visualization system determines first input data (e.g., machine learning input data 254) for at least one first machine learning model (e.g., at least one machine learning model 256) based on the first electronic data of the user. In some embodiments, a machine learning input data engine (e.g., machine learning input data engine 210) determines the first input data.

In step 1108, the machine learning-based state prediction and visualization system determines second input data (e.g., machine learning input data 254) for the at least one first machine learning model based on the first electronic data of the user. In some embodiments, a machine learning input data engine (e.g., machine learning input data engine 210) determines the second input data.

In step 1110, the machine learning-based state prediction and visualization system predicts, based on the first input data and the at least one first machine learning model (e.g., the first input data may be provided as input to the first machine learning model), a first mental state of the first user. The first mental state may comprise a set of first mood values (e.g., mood values 260), a set of first uncertainty values, and a set of a first magnitude values. Each first mood value of the set of first mood values may be associated with a corresponding first uncertainty value of the set of first uncertainty values and a corresponding first magnitude value of the set of first magnitude values. The first magnitude value may indicate a first relative strength and/or weakness of the associated first mood value. In some embodiments, a machine learning-based state prediction engine (e.g., machine learning-based state prediction engine 212) performs the prediction. In some embodiments, the predicted first mental state of the user (e.g., at a particular point of time and/or a particular period of time) may be stored by the management engine in a patient user profile (e.g., a user profile 250) and/or the datastore.

In step 1112, the machine learning-based state prediction and visualization system predicts, based on the second input data and the at least one first machine learning model (e.g., the second input data may be provided as input to the first machine learning model), a second mental state of the second user. The second mental state may comprise a set of second mood values (e.g., mood values 260), a set of second uncertainty values, and a set of second magnitude values. Each second mood value of the set of second mood values may be associated with a corresponding second uncertainty value of the set of second uncertainty values and a corresponding second magnitude value of the set of second magnitude values. The second magnitude value may indicate a second relative strength and/or weakness of the associated first mood value. In some embodiments, the machine learning-based state prediction engine performs the prediction. In some embodiments, the predicted second mental state of the second user (e.g., at a particular point of time and/or a particular period of time) may be stored by the management engine in a provider user profile (e.g., a user profile 1030) and/or machine learning-based predictive matching system datastore.

In step 1114, a machine learning-based predictive matching system (e.g., machine learning-based predictive matching system 103) determines one or more inventories of preferences (e.g., C-NIP, URICA) of the first user. Determining the one or more inventories can include determining questions of the one or more inventories, determining answers to the one or questions (e.g., in response to first user input), and/or determining an inventory score (e.g., between 1 and 100) based on the inventor questions, and the inventory answers, and/or a default inventory score calculation formula and/or model. The inventory of preferences can include one or more goals (or, criteria) of the first user. In some embodiments, a machine learning-based predictive matching engine (e.g., machine learning-based predictive matching engine 1008) determines the inventory of preferences for the first user. In some embodiments, the goals of the first inventory may be distinct (e.g., otherwise obtained by the machine learning-based predictive matching system) from the inventory of preferences. In some embodiments, the machine learning-based predictive matching engine determines the one or more inventories of preferences.

In some embodiments, the machine learning-based predictive matching system tunes the one or more inventories of preferences based on the mental state of the first user. For example, the machine learning-based predictive matching system can adjust the default inventory score calculation formula and/or model based on the mental state of the first user. In some embodiments, the machine learning-based predictive matching engine tunes the one or more inventories of preferences (e.g., prior to providing to one or more second machine learning models for predicting matches).

In step 1116, the machine learning-based predictive matching system determines one or more respective goals for each second user of the plurality of second users. In some embodiments, the machine learning-based predictive matching engine determines the one or more respective goals.

In step 1118, the machine learning-based predictive matching system obtains labeled session data (e.g., machine learning input data 1032) associated with a plurality of successful therapeutic matches. In some embodiments, the machine learning-based predictive matching engine obtains the labeled session data.

In step 1120, the machine learning-based predictive matching system generates (e.g., builds from scratch and/or builds from a template machine learning model, and/or refines a live machine learning and/or refines a template machine learning model) one or more second machine learning models (e.g., machine learning models 1034) based on the first mental state of the first user, the respective second mental state(s) of each of the plurality of second users, the inventory of preferences of the first user, the one or more respective goals of the second users of the plurality of second users, and/or the labeled session data. In some embodiments, the machine learning-based predictive matching engine and/or a feedback engine (e.g., feedback engine 1010) generates the one or more second machine learning models.

In step 1122, the machine learning-based predictive matching system predicts, based on the first mental state of the first user, the respective second mental states of the plurality of second users, the inventory of preferences of the first user, the labeled session data, and/or one or more second machine learning models, one or more matches (e.g., therapeutic matches) between the first user and one or more second users of the plurality of second users. For example, the first mental state of the first user, the respective second mental states of the plurality of second users, the inventory of preferences of the first user (e.g., an inventory score calculated using a default inventory calculation formula and/or a tuned inventory score calculated using a tuned inventory calculation formula), and/or the labeled session data may be provided as input to the one or more second machine learning models. In some embodiments, a machine learning-based predictive matching engine (e.g., machine learning-based predictive matching engine 1008) predicts the match.

In step 1124, the machine learning-based predictive matching system facilitates presentation, via a graphical user interface (GUI), of the one or more predicted therapeutic matches. In some embodiments, a presentation engine (e.g., presentation engine 1012) facilitates the presentation.

In step 1126, the machine learning-based predictive matching system receives, in response to the first user interacting with the GUI, a user selection of a particular second user of the one or more second users of the plurality of second users. In some embodiments, the presentation engine receives the user selection.

In step 1128, the machine learning-based predictive matching system automatically connects, in response to receiving the user selection of the particular second user of the one or more second users of the plurality of second users, the first user with each of the one or more second users of the plurality of second users. In some embodiments, the machine learning-based predictive matching engine performs the connecting.

Figure 12:
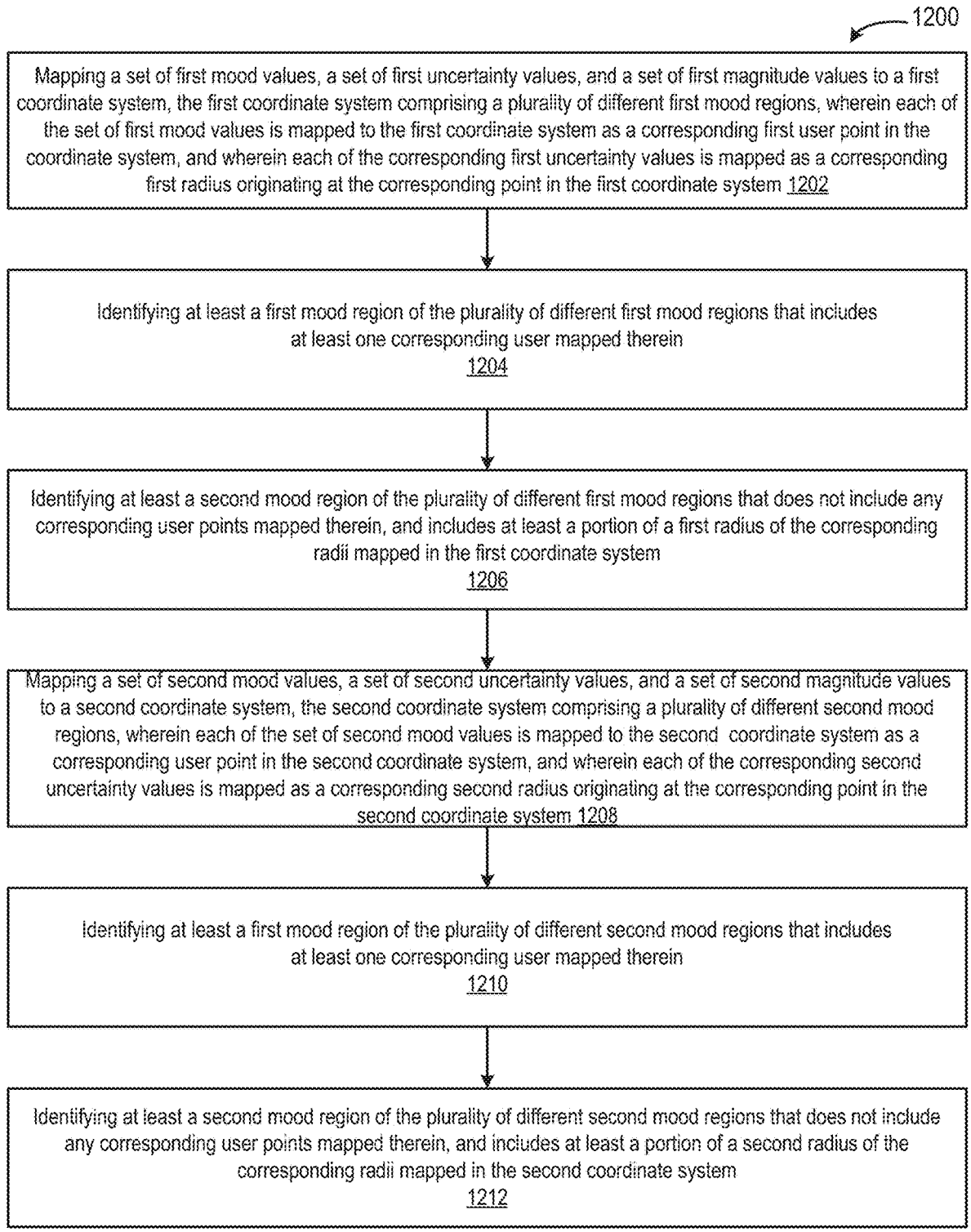
FIG. 12 depicts a flowchart of an example of a method of mental state prediction for multiple users according to some embodiments.

FIG. 12 depicts a flowchart of an example of a method 1200 of mental state prediction for multiple users (e.g., one or more patient users and/or one or more provider users) according to some embodiments. In this and other flowcharts and/or sequence diagrams, the flowchart illustrates by way of example a sequence of steps. It should be understood that some or all of the steps may be repeated, reorganized for parallel execution, and/or reordered, as applicable. Moreover, some steps that could have been included may have been removed to avoid providing too much information for the sake of clarity and some steps that were included could be removed, but may have been included for the sake of illustrative clarity.

In step 1202, a machine learning-based state prediction and visualization system (e.g., machine learning-based state prediction and visualization system 102) maps a set of first mood values (e.g., mood values 260), a set of first uncertainty values, and a set of first magnitude values to a first coordinate system (e.g., a two-dimensional coordinate system and/or three-dimensional coordinate system). The first coordinate system may comprise a plurality of different first mood regions. Each of the set of first mood values may be mapped to the first coordinate system as a corresponding first user point in the first coordinate system. Each of the corresponding first uncertainty values may be mapped as a corresponding first radius originating at the corresponding first user point in the first coordinate system. In some embodiments, a machine learning-based state prediction engine (e.g., machine learning-based state prediction engine 212) and/or visualization engine 214 performs the mapping. In some embodiments, a first mental state of a first user (e.g., user system 104 and/or a patient user of a user system 104) is defined by the mapping of step 1202 (and/or other mappings described herein) and/or vice versa. Accordingly, in some instances, the first user may have a unique mental state (e.g., different from any other user or previously known or defined mental state).

In step 1204, the machine learning-based state prediction and visualization system identifies at least a first mood region of the plurality of different mood first regions that includes at least one corresponding user mapped therein. In some embodiments, the machine learning-based state prediction engine and/or visualization engine performs the identification.

In step 1206, the machine learning-based state prediction and visualization system identifies at least a second mood region of the plurality of different first mood regions that does not include any corresponding user points mapped therein, and also includes at least a portion of a first radius of the corresponding radii mapped in the first coordinate system. In some embodiments, the machine learning-based state prediction engine and/or visualization engine performs the identification.

In some embodiments, the mental state of the first user is predicted based on the mood regions identified in steps 1204 and 1206, as well as the first magnitude values associated with the at least one corresponding first user point mapped in the at least a first mood region of the plurality of different first moods regions and the first radius of the corresponding radii mapped in the first coordinate system.

In step 1208, the machine learning-based state prediction and visualization system maps a set of second mood values (e.g., mood values 260), a set of second uncertainty values, and a set of second magnitude values to a second coordinate system (e.g., a two-dimensional coordinate system and/or three-dimensional coordinate system). In some embodiments, the second coordinate system is the same as the first coordinate system. In some embodiments, the second coordinate system is different from the first coordinate system. The second coordinate system may comprise a plurality of different second mood regions. Each of the set of second mood values may be mapped to the second coordinate system as a corresponding second user point in the second coordinate system. Each of the corresponding second uncertainty values may be mapped as a corresponding second radius originating at the corresponding second user point in the second coordinate system. In some embodiments, the machine learning-based state prediction engine and/or visualization engine 214 performs the mapping. In some embodiments, a second mental state of a second user (e.g., user system 104 and/or a patient user of a user system 104) is defined by the mapping of step 1202 (and/or other mappings described herein) and/or vice versa. Accordingly, in some instances, the second user may have a unique mental state (e.g., different from any other user or previously known or defined mental state).

In step 1210, the machine learning-based state prediction and visualization system identifies at least a first mood region of the plurality of different second mood regions that includes at least one corresponding second user mapped therein. In some embodiments, the machine learning-based state prediction engine and/or visualization engine performs the identification.

In step 1212, the machine learning-based state prediction and visualization system identifies at least a second mood region of the plurality of different second mood regions that does not include any corresponding user points mapped therein, and also includes at least a portion of a second radius of the corresponding radii mapped in the second coordinate system. In some embodiments, the machine learning-based state prediction engine and/or visualization engine performs the identification.

In some embodiments, the mental state of the first user is predicted based on the mood regions identified in steps 1210 and 1212, as well as the second magnitude values associated with the at least one corresponding second user point mapped in the at least a first mood region of the plurality of different second moods regions and the second radius of the corresponding radii mapped in the second coordinate system.

Figure 13:
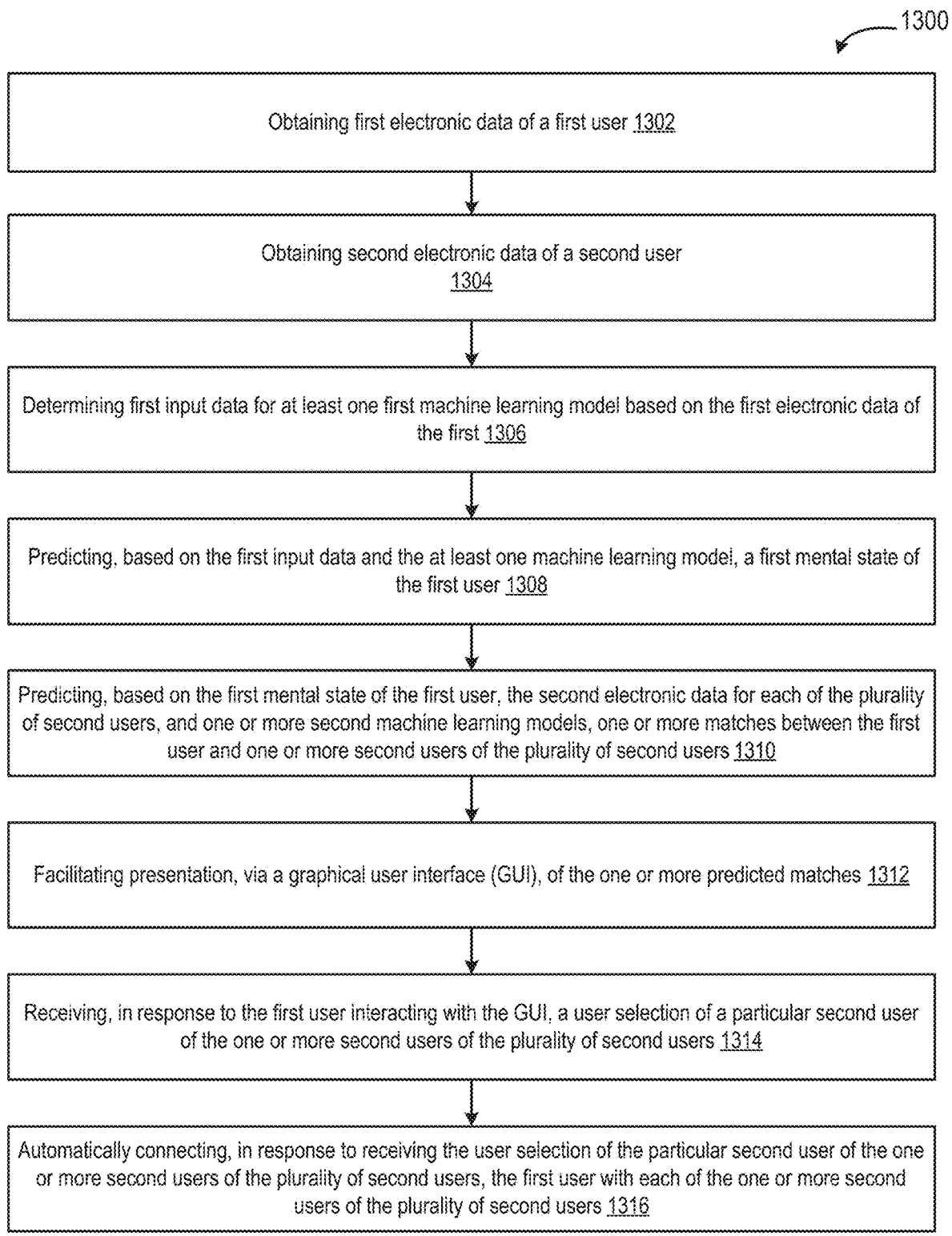
FIG. 13 depicts a flowchart of an example of a method of machine learning-based match prediction according to some embodiments.

FIG. 13 depicts a flowchart of an example of a method 1300 of machine learning-based match (e.g., therapeutic match) prediction according to some embodiments. In this and other flowcharts and/or sequence diagrams, the flowchart illustrates by way of example a sequence of steps. It should be understood that some or all of the steps may be repeated, reorganized for parallel execution, and/or reordered, as applicable. Moreover, some steps that could have been included may have been removed to avoid providing too much information for the sake of clarity and some steps that were included could be removed, but may have been included for the sake of illustrative clarity.

In step 1302, a machine learning-based state prediction and visualization system (e.g., machine learning-based state prediction and visualization system 102) obtains first electronic data (e.g., electronic data 252) of a first user (e.g., user system 104 and/or a patient user of a user system 104). In some embodiments, a communication engine (e.g., communication engine 220) and/or an electronic data collection engine (e.g., electronic data collection engine 208) obtains the first electronic data over a communication network (e.g., communication network 108) from one or more user systems (e.g., user systems 104) and/or one or more third-party systems (e.g., third-party systems 106). A management engine (e.g., management engine 202) may store the first electronic data in one or more datastores (e.g., machine learning-based state prediction and visualization system datastore 240 and/or machine learning-based predictive matching system datastore 1020).

In step 1304, the machine learning-based state prediction and visualization system obtains second electronic data (e.g., electronic data 252) for each of a plurality of second users (e.g., user systems 104 and/or provider users of the user systems 104). In some embodiments, the communication engine and/or the electronic data collection engine obtains the second electronic data over the communication network from one or more user systems (e.g., user systems 104) and/or one or more third-party systems (e.g., third-party systems 106). The management engine may store the second electronic data in the one or more datastores.

In step 1306, the machine learning-based state prediction and visualization system determines first input data (e.g., machine learning input data 254) for at least one first machine learning model (e.g., at least one machine learning model 256) based on the first electronic data of the user. In some embodiments, a machine learning input data engine (e.g., machine learning input data engine 210) determines the first input data.

In step 1308, the machine learning-based state prediction and visualization system predicts, based on the first input data and the at least one first machine learning model (e.g., the first input data may be provided as input to the first machine learning model), a first mental state of the first user. The first mental state may comprise a set of first mood values (e.g., mood values 260), a set of first uncertainty values, and a set of a first magnitude values. Each first mood value of the set of first mood values may be associated with a corresponding first uncertainty value of the set of first uncertainty values and a corresponding first magnitude value of the set of first magnitude values. The first magnitude value may indicate a first relative strength and/or weakness of the associated first mood value. In some embodiments, a machine learning-based state prediction engine (e.g., machine learning-based state prediction engine 212) performs the prediction. In some embodiments, the predicted first mental state of the user (e.g., at a particular point of time and/or a particular period of time) may be stored by the management engine in a patient user profile (e.g., a user profile 250) and/or the datastore.

In step 1310, a machine learning-based predictive matching system (e.g., machine learning-based predictive matching system 103) predicts, based on the first mental state of the first user, the second electronic data for each of the plurality of second users, and one or more second machine learning models (e.g., the first mental state of the first user, the second electronic data for each of the plurality of second users may be provides as input the one or more second machine learning models), one or more matches (e.g., therapeutic matches) between the first user and one or more second users of the plurality of second users. In some embodiments, a machine learning-based predictive matching engine (e.g., metadata processing engine 1008) predicts the one or more therapeutic matches between the first user and one or more second users of the plurality of second users.

In step 1312, the machine learning-based predictive matching system facilitates presentation, via a graphical user interface (GUI), of the one or more therapeutic matches. In some embodiments, a presentation engine (e.g., presentation engine 1012) facilitates the presentation.

In step 1314, the machine learning-based predictive matching system receives, in response to the first user interacting with the GUI, a user selection of a particular second user of the one or more second users of the plurality of second users. In some embodiments, the presentation engine receives the user selection.

Figure 14:
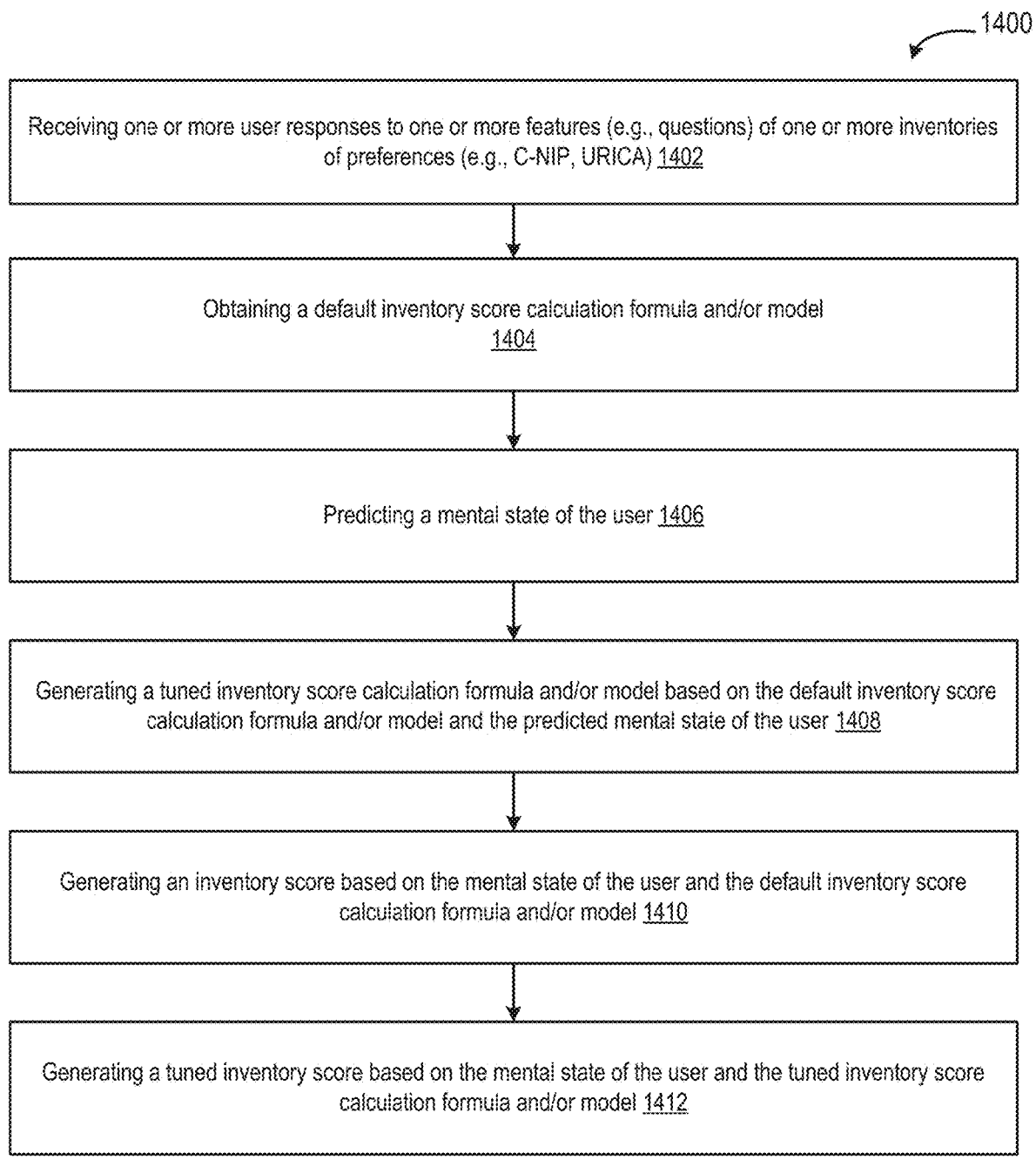
FIG. 14 depicts a flowchart of an example of a method of determining inventory preferences according to some embodiments.

In step 1316, the machine learning-based predictive matching system automatically connects, in response to receiving the user selection of the particular second user of the one or more second users of the plurality of second users, the first user with each of the one or more second users of the plurality of second users. In some embodiments, the machine learning-based predictive matching engine performs the connecting FIG. 14 depicts a flowchart of an example of a method 1400 of determining inventory preferences according to some embodiment. In this and other flowcharts and/or sequence diagrams, the flowchart illustrates by way of example a sequence of steps. It should be understood that some or all of the steps may be repeated, reorganized for parallel execution, and/or reordered, as applicable. Moreover, some steps that could have been included may have been removed to avoid providing too much information for the sake of clarity and some steps that were included could be removed, but may have been included for the sake of illustrative clarity.

In step 1402, a machine learning-based predictive matching system receives one or more user responses to one or more features (e.g., questions) of one or more inventories of preferences (e.g., C-NIP, URICA). In some embodiments, a presentation engine (e.g., presentation engine 1012) and/or communication engine (e.g., 1014) receives the one or more user responses (e.g., over communication network 108).

In step 1404, the machine learning-based predictive matching system obtains a default inventory score calculation formula and/or model. In some embodiments, a machine learning-based predictive matching engine (e.g., machine learning-based predictive matching engine 1008) obtains the default inventory score calculation formula and/or model.

In step 1406, a machine learning-based state prediction and visualization system (e.g., machine learning-based state prediction and visualization system 102) predicts a mental state of the user. In some embodiments, a machine learning-based state prediction engine (e.g., machine learning-based state prediction engine 212) predicts the mental state of the user.

In step 1408, the machine learning-based predictive matching system generates a tuned inventory score calculation formula and/or model based on the default inventory score calculation formula and/or model and the predicted mental state of the user. In some embodiments, a machine learning-based predictive matching engine (e.g., machine learning-based predictive matching engine 1008) and/or a feedback engine (e.g., feedback engine 1010) generates the tuned inventory score calculation formula and/or model.

In step 1410, the machine learning-based predictive matching system generates an inventory score based on the mental state of the user and the default inventory score calculation formula and/or model. In some embodiments, the machine learning-based predictive matching engine generates the inventory score.

In step 1410, the machine learning-based predictive matching system generates a tuned inventory score based on the mental state of the user and the tuned inventory score calculation formula and/or model. In some embodiments, the machine learning-based predictive matching engine generates the tuned inventory score.

Figure 15:
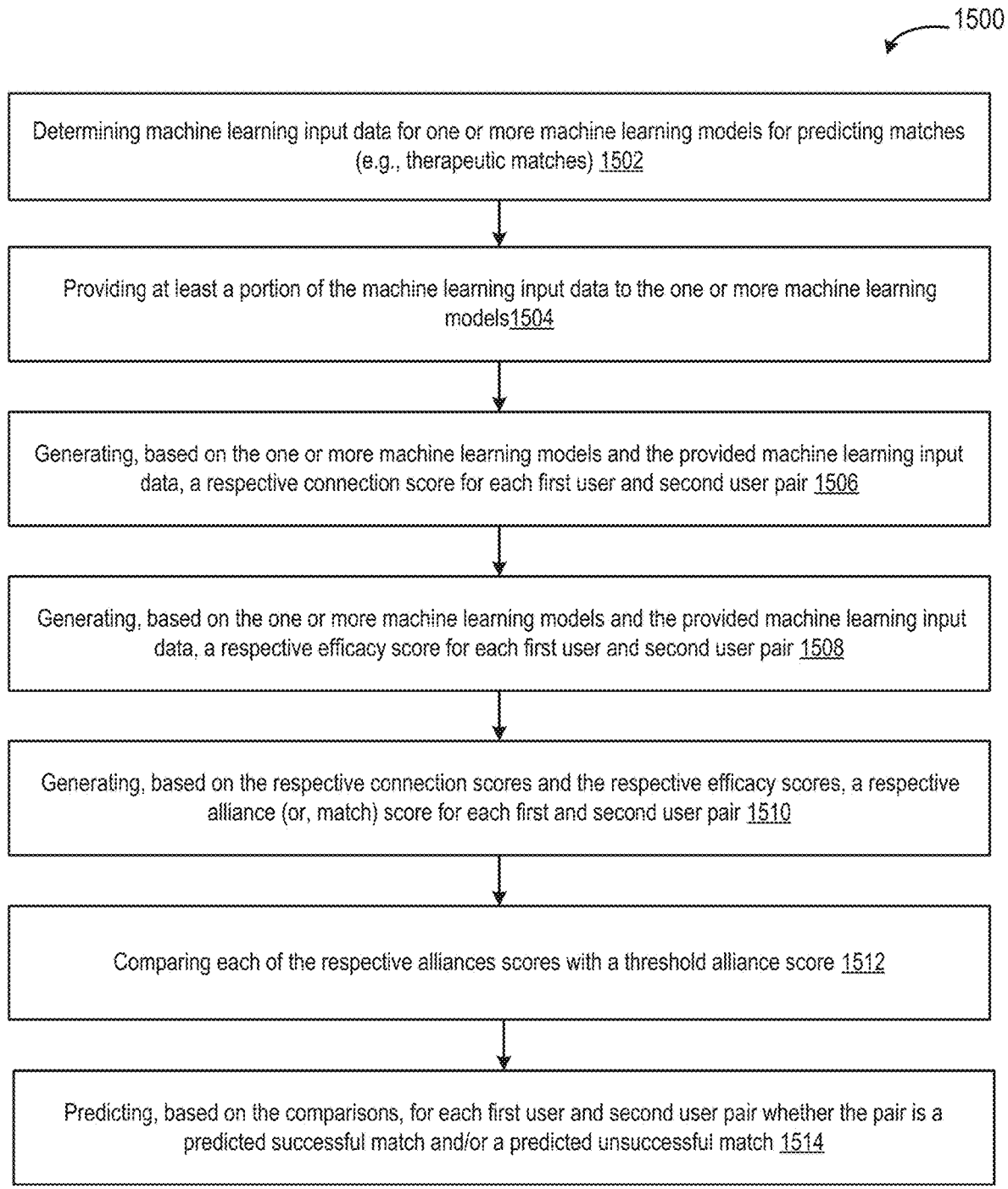
FIG. 15 depicts a flowchart of an example of a method of machine learning-based match prediction according to some embodiments.

FIG. 15 depicts a flowchart of an example of a method 1500 of machine learning-based match prediction according to some embodiments. In this and other flowcharts and/or sequence diagrams, the flowchart illustrates by way of example a sequence of steps. It should be understood that some or all of the steps may be repeated, reorganized for parallel execution, and/or reordered, as applicable. Moreover, some steps that could have been included may have been removed to avoid providing too much information for the sake of clarity and some steps that were included could be removed, but may have been included for the sake of illustrative clarity.

In step 1502, a machine learning-based predictive matching system (e.g., machine learning-based predictive matching system 103) determines machine learning input data (e.g., machine learning input data 1032) for one or more machine learning models (e.g., 1034) for predicting matches (e.g., therapeutic matches). For example, the machine learning input data can include predicted mental state(s) of a first user (e.g., a patient user), predicted mental state(s) for each of a plurality of second users (e.g., provider users), user goals (e.g., provider goals or criteria, patient goals or criteria), inventories of a preferences of the first user (e.g., C-NIP, URICA), inventory scores (e.g., default inventory scores, tuned inventory scores), and/or curated portions of some or off the aforementioned data. In some embodiments, a machine learning input data engine (e.g., machine learning input data engine 1006) determines the machine learning input data.

In step 1504, the machine learning-based predictive matching system provides at least a portion of the machine learning input data to the one or more machine learning models. In some embodiments, the machine learning input data engine provides the machine learning input data to the one or more machine learning models of a machine learning-based predictive matching engine (e.g., machine learning-based predictive matching engine 1008).

In step 1506, the machine learning-based predictive matching system generates, based on the one or more machine learning models and the provided machine learning input data, a respective connection score for each first user and second user pair. The connection score may be an output of the one or more machine learning models (e.g., a first machine learning model of the one or more machine learning models) and/or based on the output. In some embodiments, the machine learning-based predictive matching engine generates the respective connection scores.

In step 1508, the machine learning-based predictive matching system generates, based on the one or more machine learning models and the provided machine learning input data, a respective efficacy score for each first user and second user pair. The efficacy score may be an output of the one or more machine learning models (e.g., a second machine learning model of the one or more machine learning models) and/or based on the output. In some embodiments, the machine learning-based predictive matching engine generates the respective efficacy scores.

In step 1510, the machine learning-based predictive matching system generates, based on the respective connection scores and the respective efficacy scores, a respective alliance (or, match) score for each first and second user pair. In some embodiments, the machine learning-based predictive matching system generates the respective alliance scores.

In step 1512, the machine learning-based predictive matching system compares each of the respective alliances scores with a threshold alliance score. In some embodiments, the machine learning-based predictive matching engine performs the comparison.

In step 1514, the machine learning-based predictive matching engine predicts, based on the comparisons, for each first user and second user pair whether the pair is a predicted successful match and/or a predicted unsuccessful match. For example, if an alliance score satisfies the threshold alliance score (e.g., it meets or exceeds the alliance threshold score), then the machine learning-based predictive matching system may predict a successful match, and if an alliance score does not satisfy the threshold alliance score (e.g., it is below the alliance threshold score), then the machine learning-based predictive matching system may predict an unsuccessful match. In some embodiments, the machine learning-based predictive matching engine performs the prediction.

Figure 16:
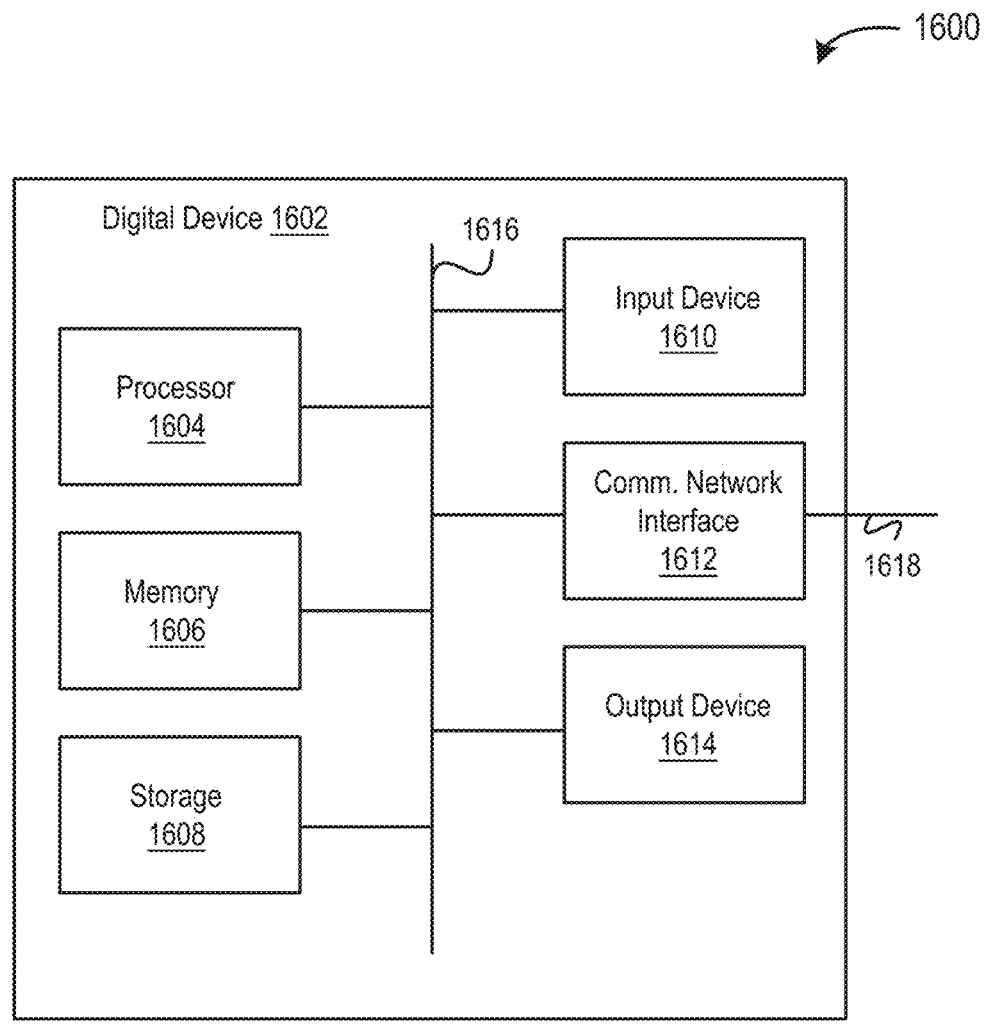
FIG. 16 is a diagram of an example computer system for implementing the features disclosed herein according to some embodiments.

FIG. 16 depicts a diagram 1600 of an example of a computing device 1602. Any of the systems, engines, datastores, and/or networks described herein may comprise an instance of one or more computing devices 1602. In some embodiments, functionality of the computing device 1602 is improved to the perform some or all of the functionality described herein. The computing device 1602 comprises a processor 1604, memory 1606, storage 1608, an input device 1610, a communication network interface 1612, and an output device 1614 communicatively coupled to a communication channel 1616. The processor 1604 is configured to execute executable instructions (e.g., programs). In some embodiments, the processor 1604 comprises circuitry or any processor capable of processing the executable instructions.

The memory 1606 stores data. Some examples of memory 1606 include storage devices, such as RAM, ROM, RAM cache, virtual memory, etc. In various embodiments, working data is stored within the memory 1606. The data within the memory 1606 may be cleared or ultimately transferred to the storage 1608.

The storage 1608 includes any storage configured to retrieve and store data. Some examples of the storage 1608 include flash drives, hard drives, optical drives, cloud storage, and/or magnetic tape. Each of the memory system 1606 and the storage system 1608 comprises a computer-readable medium, which stores instructions or programs executable by processor 1604.

The input device 1610 is any device that inputs data (e.g., mouse and keyboard). The output device 1614 outputs data (e.g., a speaker or display). It will be appreciated that the storage 1608, input device 1610, and output device 1614 may be optional. For example, the routers/switchers may comprise the processor 1604 and memory 1606 as well as a device to receive and output data (e.g., the communication network interface 1612 and/or the output device 1614).

The communication network interface 1612 may be coupled to a network (e.g., network 108) via the link 1618. The communication network interface 1612 may support communication over an Ethernet connection, a serial connection, a parallel connection, and/or an ATA connection. The communication network interface 1612 may also support wireless communication (e.g., 802.11 a/b/g/n, WiMax, LTE, WiFi). It will be apparent that the communication network interface 1612 may support many wired and wireless standards.

It will be appreciated that the hardware elements of the computing device 1602 are not limited to those depicted in FIG. 16. A computing device 1602 may comprise more or less hardware, software and/or firmware components than those depicted (e.g., drivers, operating systems, touch screens, biometric analyzers, and/or the like). Further, hardware elements may share functionality and still be within various embodiments described herein. In one example, encoding and/or decoding may be performed by the processor 1604 and/or a co-processor located on a GPU (i.e., NVidia).

It will be appreciated that an "engine," "system," "datastore," and/or "database" may comprise software, hardware, firmware, and/or circuitry. In one example, one or more software programs comprising instructions capable of being executable by a processor may perform one or more of the functions of the engines, datastores, databases, or systems described herein. In another example, circuitry may perform the same or similar functions. Alternative embodiments may comprise more, less, or functionally equivalent engines, systems, datastores, or databases, and still be within the scope of present embodiments. For example, the functionality of the various systems, engines, datastores, and/or databases may be combined or divided differently. The datastore or database may include cloud storage. It will further be appreciated that the term "or," as used herein, may be construed in either an inclusive or exclusive sense.

Moreover, plural instances may be provided for resources, operations, or structures described herein as a single instance.

The datastores described herein may be any suitable structure (e.g., an active database, a relational database, a self-referential database, a table, a matrix, an array, a flat file, a documented-oriented storage system, a non-relational No-SQL system, and the like), and may be cloud-based or otherwise.

The systems, methods, engines, datastores, and/or databases described herein may be at least partially processor-implemented, with a particular processor or processors being an example of hardware. For example, at least some of the operations of a method may be performed by one or more processors or processor-implemented engines. Moreover, the one or more processors may also operate to support performance of the relevant operations in a "cloud computing" environment or as a "software as a service" (SaaS). For example, at least some of the operations may be performed by a group of computers (as examples of machines including processors), with these operations being accessible via a network (e.g., the Internet) and via one or more appropriate interfaces (e.g., an Application Program Interface (API)).

The performance of certain of the operations may be distributed among the processors, not only residing within a single machine, but deployed across a number of machines. In some example embodiments, the processors or processor-implemented engines may be located in a single geographic location (e.g., within a home environment, an office environment, or a server farm). In other example embodiments, the processors or processor-implemented engines may be distributed across a number of geographic locations.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

The present invention(s) are described above with reference to example embodiments. It will be apparent to those skilled in the art that various modifications may be made and other embodiments may be used without departing from the broader scope of the present invention(s). Therefore, these and other variations upon the example embodiments are intended to be covered by the present invention(s).

What is claimed is:

1. A computing system comprising:
   one or more processors; and
   memory storing instructions that, when executed by the one or more processors, cause the computing system to perform:
   obtaining first electronic data of a first user;
   obtaining second electronic data for each of a plurality of second users;
   determining first input data for at least one first machine learning model based on the first electronic data of the first user;
   predicting, based on the first input data and the at least one first machine learning model, a first mental state of the first user, the first mental state comprising a set of first mood values, a set of first uncertainty values, and a set of first magnitude values, each first mood value of the set of first mood values being associated with a corresponding first uncertainty value of the set of first uncertainty values and a corresponding first magnitude value of the set of first magnitude values, the first magnitude value indicating a first relative strength or weakness of the associated first mood value;
   predicting, based on the first mental state of the first user, the second electronic data for each of the plurality of second users, and one or more second machine learning models, one or more therapeutic matches between the first user and one or more second users of the plurality of second users;
   facilitating presentation, via a graphical user interface (GUI), of the one or more predicted therapeutic matches;
   receiving, in response to the first user interacting with the GUI, a user selection of a particular second user of the one or more second users of the plurality of second users; and
   automatically connecting, in response to receiving the user selection of the particular second user of the one or more second users of the plurality of second users, the first user with each of the one or more second users of the plurality of second users.

2. The system of claim 1, wherein the instructions, when executed by the one or more processors, cause the computing system to perform:
   determining second input data for at least one first machine learning model based on the second electronic data for each of the plurality of second users;
   predicting, based on the second input data and the at least one first machine learning model, a respective second mental state of each of the second users of the plurality of second users, each of the respective second mental states comprising a set of second mood values, a set of second uncertainty values, and a set of second magnitude values, each second mood value of the set of second mood values being associated with a corresponding second uncertainty value of the set of second uncertainty values and a corresponding second magnitude value of the set of second magnitude values, the second magnitude value indicating a second relative strength or weakness of the associated second mood value;
   determining one or more inventories of preferences of the first user, wherein the inventories of preferences include one or more goals of the first user;
   determining one or more respective goals for each second user of the plurality of second users;
   obtaining labeled session data associated with a plurality of successful therapeutic matches; and
   generating the one or more second machine learning models based on the first mental state of the first user, the respective second mental state of each of the plurality of second users, the inventory of preferences of the first user, the one or more respective goals for each second user of the plurality of second users, and the labeled session data.

3. The system of claim 2, wherein the predicting, based on the first mental state of the first user, the second electronic data for each of the plurality of second users, and one or more second machine learning models, one or more therapeutic matches between the first user and one or more second users of the plurality of second users comprises:
  predicting, based on the first mental state of the first user, a respective second mental state of each of the plurality of second users, the one or more inventories of preferences of the first user, the one or more goals of the second user, the labeled session data associated with a plurality of successful therapeutic matches, and one or more second machine learning models, one or more therapeutic matches between the first user and one or more second users of the plurality of second users.

4. The system of claim 1, wherein the first electronic data includes text messages sent by the first user, email messages sent by the first user, voice data of the first user, image data of the first user, and one or more physical orientations of a device of the first user.

5. The system of claim 1, wherein the second electronic data includes text messages sent by the second user, email messages sent by the second user, voice data of the second user, image data of the second user, and one or more physical orientations of a device of the second user.

6. The system of claim 1, wherein the predicting, based on the first input data and the at least one first machine learning model, the first mental state of the first user further causes the computing system to perform:
  mapping the set of first mood values, the set of first uncertainty values, and the set of first magnitude values to a first coordinate system, the first coordinate system comprising a plurality of different first mood regions, wherein each of the set of first mood values is mapped to the first coordinate system as a corresponding first user point in the first coordinate system, and wherein each of the corresponding first uncertainty values is mapped as a corresponding first radius originating at the corresponding first user point in the first coordinate system;
  identifying at least a first mood region of the plurality of different first mood regions that includes at least one corresponding user mapped therein; and
  identifying at least a second mood region of the plurality of different first mood regions that does not include any corresponding user points mapped therein, and includes at least a portion of a first radius of the corresponding radii mapped in the first coordinate system;
  wherein the first mental state of the first user is predicted based on the identified at least a first mood region of the plurality of different first mood regions, the identified at least a second mood region of the plurality of different first mood regions, the first magnitude values associated with the at least one corresponding user point mapped in the at least a first mood region of the plurality of different first mood regions, and the first radius of the corresponding radii mapped in the first coordinate system.

7. The system of claim 6, wherein the first coordinate system comprises a two-dimensional coordinate system.

8. The system of claim 6, wherein the first coordinate system comprises a three-dimensional coordinate system.

9. The system of claim 6, wherein each first mood value of the set of first mood values is associated with a corresponding point in time.

10. The system of claim 6, wherein the predicting, based on the second input data and the at least one first machine learning model, a respective second mental state of each of the second users of the plurality of second users further causes the computing system to perform for each of the second users of the plurality of second users:
  mapping the set of second mood values, the set of second uncertainty values, and the set of second magnitude values to a second coordinate system, the second coordinate system comprising a plurality of different second mood regions, wherein each of the set of second mood values is mapped to the second coordinate system as a corresponding second user point in the second coordinate system, and wherein each of the corresponding second uncertainty values is mapped as a corresponding second radius originating at the corresponding second user point in the second coordinate system;
  identifying at least a first mood region of the plurality of different second mood regions that includes at least one corresponding user mapped therein; and
  identifying at least a second mood region of the plurality of different second mood regions that does not include any corresponding user points mapped therein, and includes at least a portion of a second radius of the corresponding radii mapped in the second coordinate system;
  wherein the second mental state of the second user is predicted based on the identified at least a first mood region of the plurality of different second mood regions, the identified at least a second mood region of the plurality of different second mood regions, the second magnitude values associated with the at least one corresponding user point mapped in the at least a first mood region of the plurality of different second mood regions, and the second radius of the corresponding radii mapped in the second coordinate system.

11. A method being implemented by a computing system including one or more physical processors and storage media storing machine-readable instructions, the method comprising:
  obtaining first electronic data of a first user;
  obtaining second electronic data for each of a plurality of second users;
  determining first input data for at least one first machine learning model based on the first electronic data of the first user;
  predicting, based on the first input data and the at least one first machine learning model, a first mental state of the first user, the first mental state comprising a set of first mood values, a set of first uncertainty values, and a set of first magnitude values, each first mood value of the set of first mood values being associated with a corresponding first uncertainty value of the set of first uncertainty values and a corresponding first magnitude value of the set of first magnitude values, the first magnitude value indicating a first relative strength or weakness of the associated first mood value;
  predicting, based on the first mental state of the first user, the second electronic data for each of the plurality of second users, and one or more second machine learning models, one or more therapeutic matches between the first user and one or more second users of the plurality of second users;
  facilitating presentation, via a graphical user interface (GUI), of the one or more predicted therapeutic matches;
  receiving, in response to the first user interacting with the GUI, a user selection of a particular second user of the one or more second users of the plurality of second users; and
  automatically connecting, in response to receiving the user selection of the particular second user of the one or more second users of the plurality of second users, the first user with each of the one or more second users of the plurality of second users.

12. The method of claim 11, further comprising:
determining second input data for at least one first machine learning model based on the second electronic data for each of the plurality of second users;
predicting, based on the second input data and the at least one first machine learning model, a respective second mental state of each of the second users of the plurality of second users, each of the respective second mental states comprising a set of second mood values, a set of second uncertainty values, and a set of second magnitude values, each second mood value of the set of second mood values being associated with a corresponding second uncertainty value of the set of second uncertainty values and a corresponding second magnitude value of the set of second magnitude values, the second magnitude value indicating a second relative strength or weakness of the associated second mood value;
determining one or more inventories of preferences of the first user, wherein the inventories of preferences include one or more goals of the first user;
determining one or more respective goals for each second user of the plurality of second users;
obtaining labeled session data associated with a plurality of successful therapeutic matches; and
generating the one or more second machine learning models based on the first mental state of the first user, the respective second mental state of each of the plurality of second users, the inventory of preferences of the first user, the one or more respective goals for each second user of the plurality of second users, and the labeled session data.

13. The method of claim 12, wherein the predicting, based on the first mental state of the first user, the second electronic data for each of the plurality of second users, and one or more second machine learning models, one or more therapeutic matches between the first user and one or more second users of the plurality of second users comprises:
predicting, based on the first mental state of the first user, a respective second mental state of each of the plurality of second users, the one or more inventories of preferences of the first user, the one or more goals of the second user, the labeled session data associated with a plurality of successful therapeutic matches, and one or more second machine learning models, one or more therapeutic matches between the first user and one or more second users of the plurality of second users.

14. The method of claim 11, wherein the first electronic data includes text messages sent by the first user, email messages sent by the first user, voice data of the first user, image data of the first user, and one or more physical orientations of a device of the first user.

15. The method of claim 11, wherein the second electronic data includes text messages sent by the second user, email messages sent by the second user, voice data of the second user, image data of the second user, and one or more physical orientations of a device of the second user.

16. The method of claim 11, further comprising:
mapping the set of first mood values, the set of first uncertainty values, and the set of first magnitude values to a first coordinate system, the first coordinate system comprising a plurality of different first mood regions, wherein each of the set of first mood values is mapped to the first coordinate system as a corresponding first user point in the first coordinate system, and wherein each of the corresponding first uncertainty values is mapped as a corresponding first radius originating at the corresponding first user point in the first coordinate system;
identifying at least a first mood region of the plurality of different first mood regions that includes at least one corresponding user mapped therein; and
identifying at least a second mood region of the plurality of different first mood regions that does not include any corresponding user points mapped therein, and includes at least a portion of a first radius of the corresponding radii mapped in the first coordinate system;
wherein the first mental state of the first user is predicted based on the identified at least a first mood region of the plurality of different first mood regions, the identified at least a second mood region of the plurality of different first mood regions, the first magnitude values associated with the at least one corresponding user point mapped in the at least a first mood region of the plurality of different first mood regions, and the first radius of the corresponding radii mapped in the first coordinate system.

17. The method of claim 16, wherein the first coordinate system comprises a two-dimensional coordinate system.

18. The method of claim 16, wherein the first coordinate system comprises a three-dimensional coordinate system.

19. The method of claim 16, wherein each first mood value of the set of first mood values is associated with a corresponding point in time.

20. The method of claim 16, further comprising:
mapping the set of second mood values, the set of second uncertainty values, and the set of second magnitude values to a second coordinate system, the second coordinate system comprising a plurality of different second mood regions, wherein each of the set of second mood values is mapped to the second coordinate system as a corresponding second user point in the second coordinate system, and wherein each of the corresponding second uncertainty values is mapped as a corresponding second radius originating at the corresponding second point in the second coordinate system;
identifying at least a first mood region of the plurality of different second mood regions that includes at least one corresponding user mapped therein; and
identifying at least a second mood region of the plurality of different second mood regions that does not include any corresponding user points mapped therein, and includes at least a portion of a second radius of the corresponding radii mapped in the second coordinate system;
wherein the second mental state of the second user is predicted based on the identified at least a first mood region of the plurality of different second mood regions, the identified at least a second mood region of the plurality of different second mood regions, the second magnitude values associated with the at least one corresponding user point mapped in the at least a first mood region of the plurality of different second mood regions, and the second radius of the corresponding radii mapped in the second coordinate system.

* * * * *